US012329583B2

(12) United States Patent
Seo et al.

(10) Patent No.: US 12,329,583 B2
(45) Date of Patent: Jun. 17, 2025

(54) METHOD FOR PROVIDING INFORMATION FOR CHOOSING BREAST CANCER TREATMENT METHOD BY USING BREAST CANCER ULTRASONIC IMAGE AND GENE INFORMATION

(71) Applicants: KOREA UNIVERSITY RESEARCH AND BUSINESS FOUNDATION, Seoul (KR); CHA UNIVERSITY INDUSTRY-ACADEMIC COOPERATION FOUNDATION, Gyeonggi-do (KR)

(72) Inventors: Bo Kyoung Seo, Seoul (KR); Mi-Ryung Han, Seoul (KR); Ah Young Park, Gyeonggi-do (KR)

(73) Assignees: KOREA UNIVERSITY RESEARCH AND BUSINESS FOUNDATION, Seoul (KR); CHA UNIVERSITY INDUSTRY-ACADEMIC COOPERATION FOUNDATION, Gyeonggi-do (KR)

( * ) Notice: Subject to any disclaimer, the term of this patent is extended or adjusted under 35 U.S.C. 154(b) by 667 days.

(21) Appl. No.: 17/771,939

(22) PCT Filed: Sep. 18, 2020

(86) PCT No.: PCT/KR2020/012592
§ 371 (c)(1),
(2) Date: Apr. 26, 2022

(87) PCT Pub. No.: WO2021/054752
PCT Pub. Date: Mar. 25, 2021

(65) Prior Publication Data
US 2022/0401077 A1    Dec. 22, 2022

(30) Foreign Application Priority Data

Sep. 20, 2019 (KR) .................. 10-2019-0116230

(51) Int. Cl.
*A61B 8/00* (2006.01)
*A61B 8/08* (2006.01)
(52) U.S. Cl.
CPC .......... *A61B 8/5223* (2013.01); *A61B 8/0825* (2013.01); *A61B 8/0891* (2013.01); *A61B 8/481* (2013.01)
(58) Field of Classification Search
None
See application file for complete search history.

(56) References Cited

U.S. PATENT DOCUMENTS

2014/0107936 A1* 4/2014 Janevski ................ G16B 20/20
702/19

FOREIGN PATENT DOCUMENTS

| JP | 2010-538609 A | 12/2010 |
| KR | 10-2015-0003450 A | 1/2015 |
| KR | 10-2015-0043898 A | 4/2015 |

OTHER PUBLICATIONS

Zhang et al., "Identifying ultrasound and clinical feature of breast cancer molecular subtypes by ensemble decision". Sci. Rep. 5: 11085, pp. 1-14, 2015. (Year: 2015).*

(Continued)

*Primary Examiner* — Yi-Shan Yang
(74) *Attorney, Agent, or Firm* — Harness, Dickey & Pierce, P.L.C.

(57) ABSTRACT

The present invention relates to: a method for providing information for choosing a breast cancer treatment method by using a breast cancer ultrasonic image and gene information; a system for choosing a breast cancer treatment method by using a breast cancer ultrasonic image; and a method for providing information required for predicting the prognosis of a breast cancer patient.

3 Claims, 10 Drawing Sheets

(56) References Cited

OTHER PUBLICATIONS

Xiao et al., "Superb microvascular imaging in diagnosis of breast lesions: a comparative study with contrast-enhanced ultrasonographic microvascular imaging". Br. J Radiol. 2016; 89: 20160546 (Year: 2016).*
Kettenbach et al., "Computer-assisted quantitative assessment of power Doppler US: effects of microbubble contrast agnet in the differentiation of breast tumors". European Journal of Radiology 53 (2005) 238-244 (Year: 2005).*
Dreyer et al., "Feasibility and clinical utility of endoscopic ultrasound guided biopsy of pancreatic cancer for next-generation molecular profiling". Chinese Clinical Oncology 2019; 8(2):16. (Year: 2019).*
International Search Report from corresponding PCT Application No. PCT/KR2020/012592, dated Jun. 8, 2021.
Zhang, L., et al.; "Identifying ultrasound and clinical features of breast cancer molecular subtypes by ensemble decision", Scientific Reports, vol. 5, Article No. 11085, pp. 1-14, Jun. 5, 2015.
Park, A. Y., et al.; "A Prospective Study on the Value of Ultrasound Microflow Assessment to Distinguish Malignant from Benign Solid Breast Masses: Association between Ultrasound Parameters and Hisologic Microvessel Densities", Korean Journal of Radiology, vol. 20, Issue 5, pp. 759-772, Apr. 11, 2019.
Park, A. Y., et al.; "Up-to-date Doppler techniques for breast tumor vascularity: superb microvascular imaging and contrast-enhanced ultrasound". Ultrasonography. Apr. 2018;37(2): 98-106.

* cited by examiner

METHOD FOR PROVIDING INFORMATION FOR CHOOSING BREAST CANCER TREATMENT METHOD BY USING BREAST CANCER ULTRASONIC IMAGE AND GENE INFORMATION

CROSS-REFERENCE TO RELATED APPLICATIONS

This application is a national phase application of PCT Application No. PCT/KR2020/012592, filed on Sep. 18, 2020, which claims the benefit and priority to Korean Patent Application No. 10-2019-0116230, filed on Sep. 20, 2019. The entire disclosures of the applications identified in this paragraph are incorporated herein by references.

TECHNICAL FIELD

The present disclosure was made with the support of the Ministry of Science and ICT of the Republic of Korea under Project No. 1711049499, which was conducted in the research project entitled "Development of RADIOMICS System to Predict Tumor Hypoxia and Angiogenesis in Breast Cancers" in the research program named "Personal Basic Research (Ministry of Science, ICT and Future Planning)" by Korea University under the management of the National Research Foundation of Korea, from 1 Mar. 2017 to 28 Feb. 2018.

The present disclosure was also made with the support of the Ministry of Science and ICT of the Republic of Korea under Project No. 1711069290, which was conducted in the research project entitled "Development of RADIOMICS System to Predict Tumor Hypoxia and Angiogenesis in Breast Cancers" in the research program named "Personal Basic Research (Ministry of Science and ICT) (R&D)" by Korea University under the management of the National Research Foundation of Korea, from 1 Mar. 2018 to 28 Feb. 2019.

The present disclosure was also made with the support of the Ministry of Science and ICT of the Republic of Korea under Project No. 1711085148, which was conducted in the research project entitled "Development of RADIOMICS System to Predict Tumor Hypoxia and Angiogenesis in Breast Cancers" in the research program named "Personal Basic Research (Ministry of Science and ICT) (R&D)" by Korea University under the management of the National Research Foundation of Korea, from 1 Mar. 2019 to 29 Feb. 2020.

The present disclosure relates to a method for providing information for choosing a breast cancer therapy by using an ultrasound image of breast cancer and gene information, a system for choosing a breast cancer therapy by using an ultrasound image of breast cancer, and a method for providing information needed for prediction of prognosis of a breast cancer patient.

BACKGROUND ART

Breast cancer is a group of diseases having heterogeneous causes and resulting from the accumulation of complicate genetic alternations. The development of DNA microarray analysis allows for identification of distinct molecular subtypes of breast cancer in terms of different genetic alterations and biologic behavior and has led to targeted therapy, heterogeneity of disease processes, and response to therapy, which are not fully explained by the molecular subtype of breast cancer.

The development of high-throughput sequencing technology, called next-generation sequencing (hereinafter, NGS), enables comprehensive characterization of breast cancer genome, identification of subtype-specific genetic variations, and an access to individualized therapy. RNA sequencing by using the NGS technique provides whole-transcriptome profiling with the advantage of single nucleotide resolution, increased sensitivity to detect rare sequences, and quantitative analysis of RNA expression levels.

Recent radiogenomic approaches allow the understanding of tumor heterogeneity at a genetic level to breast cancer and the discovery of image surrogates of genetic variation. It was reported in the initial radiogenomic investigation that 21 of 26 magnetic resonance (hereinafter, MR) imaging phenotypes were generally correlated with 71% (3717 of 5231) of breast cancer genes and several imaging phenotypes were correlated with individual gene sets related to breast cancer or prognostic genes. Most of subsequent investigations focused on the correlation between MR imaging features and individual genes, molecular subtypes, or recurrence score on the basis of multiple gene assays.

Recent advances in vascular ultrasound techniques, such as superb microvascular imaging (SMI) and contrast-enhanced ultrasound (CEUS), can provide microvascular information regarding breast cancer and predict tumor angiogenesis, which is a histopathological change necessary for cancer development and growth.

Several investigations demonstrated that malignant microvascular features on ultrasound imaging were associated with histologic biomarkers, such as tumor grade, tumor size, estrogen receptor (ER) positivity, human epidermal growth factor receptor 2 (HER2) overexpression, and microvessel density. From these results, vascular feature ultrasound images enable the prediction of histologic aggressiveness, and moreover the prediction of variations and relevance of particular genes related to breast cancer.

However, there is no radiogenomic research on the correlations between ultrasound (hereinafter, US) imaging phenotypes and gene expression analysis in breast cancer patients.

SUMMARY

Technical Problem

The present inventors investigated the relationship between ultrasound morphology and vascular phenotypes and genetic alteration of breast cancers using RNA sequencing, and then verified that ultrasound morphology and vascular phenotypes are related to breast cancer-associated genes capable of predicting the hormone receptor status, angiogenesis or prognosis, and drug target.

Therefore, an aspect of the present disclosure is to provide a method for providing information for choosing a breast cancer therapy by using an ultrasound image of breast cancer.

Another aspect of the present disclosure is to provide a method for providing information needed for prediction of prognosis of a breast cancer patient by using an ultrasound image of breast cancer.

Solution to Problem

The present inventors investigated the relationship between ultrasound morphology and vascular phenotypes and genetic alteration of breast cancers using RNA sequencing, and then verified that ultrasound morphology and vascular phenotypes are related to breast cancer-associated genes capable of predicting the hormone receptor status, angiogenesis or prognosis, and drug target.

The present disclosure relates to a method for providing information for choosing a breast cancer therapy by using an ultrasound image of breast cancer and a method for providing information needed for prediction of prognosis of a breast cancer patient.

Hereinafter, the present disclosure will be described in more detail.

The present inventors prospectively analyzed B-mode and vascular ultrasound images in 31 breast cancer patients. B-mode features included size, shape, echo pattern, orientation, margin, and calcifications of breast cancer. Vascular features were evaluated by vascular index, vessel morphology, distribution, penetrating vessels, enhancement degree, enhancement order, margin, internal homogeneity, and perfusion defect in SMI and contrast-enhanced ultrasound. RNA sequencing was conducted with total RNA obtained from a surgical specimen by using next-generation sequencing. The imaging features were compared with gene expression profiles, and ingenuity pathway analysis was used to identify gene networks and analyze enriched functions and canonical pathways associated with breast cancer.

An aspect of the present disclosure is directed to a method for providing information for choosing a breast cancer therapy by using an ultrasound image of breast cancer, the method including:
a phenotype determination step of determining a phenotype of a tumor by using an ultrasound image;
a gene information determination step of determining at least one gene information related to breast cancer by using the phenotype of the tumor; and
a therapy determination step of determining an individual breast cancer therapy by correlating the determined gene information with gene information associated with a breast cancer therapy.

In the present disclosure, the ultrasound image may be at least one selected from the group consisting of a B-mode ultrasound image, a superb microvascular imaging (SMI) ultrasound image, and a contrast-enhanced ultrasound (CEUS) image, and may include, for example, a B-mode ultrasound image, an SMI ultrasound image, and a contrast-enhanced ultrasound image.

The bright mode (B-mode) ultrasound image of the present disclosure corresponds to a method of displaying a reflected sound as the brightness of a dot, and is currently used in most ultrasound diagnostic equipment. The brightness of each dot is proportional to the amplitude of the reflected signal.

In the present disclosure, the phenotype determined through the B-mode ultrasound image may be at least one selected from the group consisting of size, shape, orientation, margin, and calcifications, and may include, for example, size, shape, orientation, margin, and calcifications.

In the present disclosure, the size may be related to at least one gene selected from the group consisting of MIR941-1, IGLV6-57, HIST1H1B, HIST1H3I, ADH1B, PLIN4, and LUZP6, but is not limited thereto.

In the present disclosure, sizes may be classified into less than 20 mm and 20 mm or more on the basis of the largest diameter of a tumor.

In the tumor size being 20 mm or more, the expressions of MIR941-1, IGLV6-57, HIST1H1B, and HIST1H3I genes were upregulated and the expressions of ADH1B, PLIN4, and LUZP6 genes were downregulated, compared with gene expression when the tumor size was less than 20 mm.

The tumor sizes were classified on the basis of the largest diameter of the tumor on the B-mode ultrasound.

In the present disclosure, the shape may be related to at least one gene selected from the group consisting of MIR941-1, ZFP36L1, SNHG9, H2AFY2, POTEI, UBE2Q2L, FABP7, IGHV3-43, IGKJ5, and IGKJ2, but is not limited thereto.

In the tumor shape being irregular, the expressions of MIR941-1, ZFP36L1, and SNHG9 genes were upregulated, and the expressions of H2AFY2, POTEI, UBE2Q2L, FABP7, IGHV3-43, IGKJ5, and IGKJ2 were downregulated, compared with gene expression when the tumor shape was oval.

In tumor shapes, an oval shape (e.g., an egg shape) or a circular shape was classified as an oval shape, and a shape of being not oval or circular was classified as an irregular shape.

In the present disclosure, the orientation may be related to at least one gene selected from the group consisting of TFF1, AREG, AGR3, TFF3, LINC00993, IGKV2-28, IGLV1-51, IGHV3-73, IGKV3-20, IGLV2-14, IGKV1-12, IGHV4-61, IGKV3D-15, IGHV1-3, IGHV4-4, IGHV1-18, IGHV4-34, IGHV3-74, CALML5, IGHJ5, and IGKJ2, but is not limited thereto.

In the tumor orientation being not parallel, the expressions of TFF1, AREG, AGR3, TFF3, and LINC00993 were upregulated, and the expressions of IGKV2-28, IGLV1-51, IGHV3-73, IGKV3-20, IGLV2-14, IGKV1-12, IGHV4-61, IGKV3D-15, IGHV1-3, IGHV4-4, IGHV1-18, IGHV4-34, IGHV3-74, CALML5, IGHJ5, and IGKJ2 were downregulated, compared with gene expression when the tumor orientation was parallel.

The tumor orientation was classified as parallel when the major axis of the tumor was parallel with the skin, and as not parallel when the major axis of the tumor was not parallel with the skin.

In the present disclosure, the margin may be related to HLA-C gene, but is not limited thereto.

In the tumor margin being angular, microlobulated, or spiculated, the expression of HLA-C gene was upregulated compared with gene expression when the tumor margin was indistinct.

The tumor margin was classified as indistinct when the margin was not distinct from surrounding tissues, as angular when a portion of the margin was angular, as microlobulated when the margin has a small wave shape, and as spiculated when the margin was formed of thin lines extending radially from the tumor.

In the present disclosure, the calcifications may be related to at least one gene selected from the group consisting of CALML3, HIST1H4F, IGHV4OR15-8, CCL19, and IGLV8-61, but is not limited thereto.

In the presence of the tumor calcifications, the expressions of CALML3, HIST1H4F, IGHV4OR15-8, CCL19, and IGLV8-61 were downregulated, compared with gene expression in the absence of the tumor calcifications.

The calcifications were classified as present when there were echogenic dots thought to be calcifications inside or around the tumor, and as absent otherwise.

In the present disclosure, the phenotype determined through the SMI ultrasound image may be at least one selected from the group consisting of vascular index, vessel morphology, and penetrating vessel, and may include, for example, vessel morphology, and penetrating vessel.

In the present disclosure, the vascular index may be related to at least one gene selected from the group consisting of IGHJ5, MIR1307, IGLV6-57, HLA-C, HIST2H2BE, CALML3, IGKV6-21, OR5P3, and MIR597, but is not limited thereto.

In the vascular index being 16.1% or more, the expressions of IGHJ5, MIR1307, IGLV6-57, HLA-C, and HIST2H2BE were upregulated, and the expressions of CALML3, IGKV6-21, OR5P3, and MIR597 were downregulated, compared with gene expression when the vascular index was less than 16.1%.

The vascular index was defined as the ratio of the number of pixels for the vascular signal to the pixels for the whole tumor, and vascular indexes were classified into less than 16.1% and 16.1% or more on the basis of the mean vascular index of 31 tumors.

In the present disclosure, the vessel morphology may be related to at least one gene selected from the group consisting of HIST1H4D, TUSC1, FZD8, NMI, IGF1R, UBB, SERHL2, NFIL3, CRIPAK, SNHG20, HBA2, and SNHG12, but is not limited thereto.

In the vessel morphology being complex, the expressions of HIST1H4D, TUSC1, and FZD8 genes were upregulated, and the expressions of NMI, IGF1R, UBB, SERHL2, NFIL3, CRIPAK, SNHG20, HBA2, and SNHG12 genes were downregulated, compared with gene expression when the vessel morphology was none or simple.

The vessel morphology was classified as none or simple, such as dot-like or linear in blood flow signals, and as complex when the blood flow signals were branched or formed a complex network by interconnection of several vessels.

In the present disclosure, the penetrating vessel may be related to at least one gene selected from the group consisting of HIST1H4D, CST1, TRBC2, SLC25A2, KRT14, MFAP4, IGKV2-40, NFIL3, POTEE, POTEI, ALDH3B2, CRIPAK, IGHJ2, AREG, and IGKJ5, but is not limited thereto.

In the penetrating vessel being present, the expressions of HIST1H4D, CST1, and TRBC2 genes were upregulated, and the expressions of SLC25A2, KRT14, MFAP4, IGKV2-40, NFIL3, POTEE, POTEI, ALDH3B2, CRIPAK, IGHJ2, AREG, and IGKJ5 genes were downregulated, compared with gene expression when the penetrating vessel was absent.

The penetrating vessel was classified as present when there are vessels connecting from the outside to the insides of a tumor, and as absent otherwise.

In the present disclosure, the phenotype determined through the contrast-enhanced ultrasound image may be at least one selected from the group consisting of enhancement order, enhancement margin, internal homogeneity, penetrating vessel, and perfusion defect, and may include, for example, enhancement order, enhancement margin, internal homogeneity, penetrating vessel, and perfusion defect.

In the present disclosure, the enhancement order may be related to at least one gene selected from the group consisting of IGKV1D-39, CCL3L3, IGHG4, IGKV1D-12, IGKV3D-11, SNHG12, CPB1, MIR562, and VTRNA2-1, but is not limited thereto.

In the enhancement order being centripetal, the expressions of IGKV1D-39, CCL3L3, IGHG4, IGKV1D-12, IGKV3D-11, SNHG12, CPB1, MIR562, and VTRNA2-1 were downregulated, compared with gene expression when the enhancement order was diffuse.

The enhancement order was classified as diffuse when there was contrast enhancement overall within a tumor, and as centripetal when contrast enhancement increased from the outside to the inside of a tumor.

In the present disclosure, the enhancement margin may be related to at least one gene selected from the group consisting of STH, TFF1, STC2, AMY2A, HOXB5, IGKV1D-39, PHLDA2, HIST1H2AJ, TRAV14DV4, HIST1H1A, CXCL10, ISG15, IGHV4-39, IGKV3D-15, HIST2H2BF, HIST1H2BM, IGKV2-28, IGHV3-21, CALML5, IGHV1-18, IGKV2-29, IGHG4, IGHJ4, IGHJ5, and IGKJ2, but is not limited thereto.

In the enhancement margin being not circumscribed, the expressions of STH, TFF1, STC2, AMY2A, and HOXB5 were upregulated, and the expressions of IGKV1D-39, PHLDA2, HIST1H2AJ, TRAV14DV4, HIST1H1A, CXCL10, ISG15, IGHV4-39, IGKV3D-15, HIST2H2BF, HIST1H2BM, IGKV2-28, IGHV3-21, CALML5, IGHV1-18, IGKV2-29, IGHG4, IGHJ4, IGHJ5, and IGKJ2 were downregulated, compared with gene expression when the enhancement margin was circumscribed.

The enhancement margin was classified as circumscribed for being circumscribed, and as not circumscribed for being not circumscribed.

In the present disclosure, the internal homogeneity may be related to at least one gene selected from the group consisting of IGKJ5, HLA-DQA1, HIST1H1B, and IGHV3-74, but is not limited thereto.

In the internal homogeneity being heterogeneous, the expressions of IGKJ5, HLA-DQA1, and HIST1H1B genes were upregulated and the expression of IGHV3-74 gene was downregulated, compared with gene expression where the internal homogeneity was homogeneous.

The internal homogeneity was classified as homogeneous when there was uniform contrast enhancement inside a tumor, and as heterogeneous when there was non-uniform contrast enhancement.

In the present disclosure, the penetrating vessel may be related to at least one gene selected from the group consisting of AGR2, HIST1H2BI, IGHV4-4, IGLV3-25, IGKV1D-39, IGHV1-2, IGHV3-15, IGKV1-27, IGLV3-1, IGKV2-40, IGKV2D-40, IGHV1-18, HIST1H2AG, IGHV3-33, IGKV1-12, IGKV1-17, IGHG1, TRBV5-6, IGHG4, IGHV4-61, IGKV2-28, IGHV1-8, IGHV4-39, IGHV3-21, IGHV3-9, IGKV3D-15, MIR562, IGHV1-69, IGHV4-31, IGHV1-3, and OR2J3, but is not limited thereto.

In the penetrating vessel being present, the expression of AGR2 was upregulated, and the expressions of HIST1H2BI, IGHV4-4, IGLV3-25, IGKV1D-39, IGHV1-2, IGHV3-15, IGKV1-27, IGLV3-1, IGKV2-40, IGKV2D-40, IGHV1-18, HIST1H2AG, IGHV3-33, IGKV1-12, IGKV1-17, IGHG1, TRBV5-6, IGHG4, IGHV4-61, IGKV2-28, IGHV1-8, IGHV4-39, IGHV3-21, IGHV3-9, IGKV3D-15, MIR562, IGHV1-69, IGHV4-31, IGHV1-3, and OR2J3 were downregulated, compared with gene expression when the penetrating vessel was absent.

The penetrating vessel was classified as present when there was a blood flow signal of contrast enhancement connecting from the outside to the inside of a tumor, and as absent otherwise.

In the present disclosure, the perfusion defect may be related to at least one gene selected from the group consisting of HLA-DQA1, AREG, SNHG29, and IGHV3-74, but is not limited thereto.

In the perfusion defect being present, the expression of HLA-DQA1 gene was upregulated and the expressions of AREG, SNHG29, and IGHV3-74 genes were downregulated, compared with gene expression when the perfusion defect was absent.

The perfusion defect was classified as present when some contrast enhancement defects were shown inside a contrast-enhanced tumor, and as absent when no perfusion defect was shown.

In the present disclosure, the treatment method may be at least one selected from the group consisting of drug therapy, immunotherapy, hormone therapy, and radiation therapy, but is not limited thereto, and may include all that are used in the treatment of breast cancer.

Another aspect of the present disclosure is directed to a system for choosing a breast cancer therapy by using an ultrasound image of breast cancer, the system including:
 a database allowing gene information associated with a breast cancer therapy to be retrieved or extracted;
 a communication unit accessible to the database;
 a first determination module determining a phenotype of a tumor by using an ultrasound image;
 a second determination module determining at least one gene information related to breast cancer by using the phenotype of the tumor;
 a third determination module determining an individual breast cancer therapy by correlating the determined gene information with the gene information associated with the breast cancer therapy; and
 a display unit displaying a determination value determined by each of the determination modules.

In the present disclosure, the ultrasound image may be at least one selected from the group consisting of a B-mode ultrasound image, a superb microvascular imaging (SMI) ultrasound image, and a contrast-enhanced ultrasound (CEUS) image, and may include, for example, a B-mode ultrasound image, an SMI ultrasound image, and a contrast-enhanced ultrasound image.

In the present disclosure, the phenotype determined through the B-mode ultrasound image may be at least one selected from the group consisting of size, shape, orientation, margin, and calcifications, and may include, for example, size, shape, orientation, margin, and calcifications.

In the present disclosure, the size may be related to at least one gene selected from the group consisting of MIR941-1, IGLV6-57, HIST1H1B, HIST1H3I, ADH1B, PLIN4, and LUZP6, but is not limited thereto.

In the present disclosure, the shape may be related to at least one gene selected from the group consisting of MIR941-1, ZFP36L1, SNHG9, H2AFY2, POTEI, UBE2Q2L, FABP7, IGHV3-43, IGKJ5, and IGKJ2, but is not limited thereto.

In the present disclosure, the orientation may be related to at least one gene selected from the group consisting of TFF1, AREG, AGR3, TFF3, LINC00993, IGKV2-28, IGLV1-51, IGHV3-73, IGKV3-20, IGLV2-14, IGKV1-12, IGHV4-61, IGKV3D-15, IGHV1-3, IGHV4-4, IGHV1-18, IGHV4-34, IGHV3-74, CALML5, IGHJ5, and IGKJ2, but is not limited thereto.

In the present disclosure, the margin may be related to HLA-C gene, but is not limited thereto.

In the present disclosure, the calcifications may be related to at least one gene selected from the group consisting of CALML3, HIST1H4F, IGHV4OR15-8, CCL19, and IGLV8-61, but is not limited thereto.

In the present disclosure, the phenotype determined through the SMI ultrasound image may be at least one selected from the group consisting of vascular index, vessel morphology, and penetrating vessel, and may include, for example, vessel morphology, and penetrating vessel.

In the present disclosure, the vascular index may be related to at least one gene selected from the group consisting of IGHJ5, MIR1307, IGLV6-57, HLA-C, HIST2H2BE, CALML3, IGKV6-21, OR5P3, and MIR597, but is not limited thereto.

In the present disclosure, the vessel morphology may be related to at least one gene selected from the group consisting of HIST1H4D, TUSC1, FZD8, NMI, IGF1R, UBB, SERHL2, NFIL3, CRIPAK, SNHG20, HBA2, and SNHG12, but is not limited thereto.

In the present disclosure, the penetrating vessel may be related to at least one gene selected from the group consisting of HIST1H4D, CST1, TRBC2, SLC25A2, KRT14, MFAP4, IGKV2-40, NFIL3, POTEE, POTEI, ALDH3B2, CRIPAK, IGHJ2, AREG, and IGKJ5, but is not limited thereto.

In the present disclosure, the phenotype determined through the contrast-enhanced ultrasound image may be at least one selected from the group consisting of enhancement order, enhancement margin, internal homogeneity, penetrating vessel, and perfusion defect, and may include, for example, enhancement order, enhancement margin, internal homogeneity, penetrating vessel, and perfusion defect.

In the present disclosure, the enhancement order may be related to at least one gene selected from the group consisting of IGKV1D-39, CCL3L3, IGHG4, IGKV1D-12, IGKV3D-11, SNHG12, CPB1, MIR562, and VTRNA2-1, but is not limited thereto.

In the present disclosure, the enhancement margin may be related to at least one gene selected from the group consisting of STH, TFF1, STC2, AMY2A, HOXB5, IGKV1D-39, PHLDA2, HIST1H2AJ, TRAV14DV4, HIST1H1A, CXCL10, ISG15, IGHV4-39, IGKV3D-15, HIST2H2BF, HIST1H2BM, IGKV2-28, IGHV3-21, CALML5, IGHV1-18, IGKV2-29, IGHG4, IGHJ4, IGHJ5, and IGKJ2, but is not limited thereto.

In the present disclosure, the internal homogeneity may be related to at least one gene selected from the group consisting of IGKJ5, HLA-DQA1, HIST1H1B, and IGHV3-74, but is not limited thereto.

In the present disclosure, the penetrating vessel may be related to at least one gene selected from the group consisting of AGR2, HIST1H2BI, IGHV4-4, IGLV3-25, IGKV1D-39, IGHV1-2, IGHV3-15, IGKV1-27, IGLV3-1, IGKV2-40, IGKV2D-40, IGHV1-18, HIST1H2AG, IGHV3-33, IGKV1-12, IGKV1-17, IGHG1, TRBV5-6, IGHG4, IGHV4-61, IGKV2-28, IGHV1-8, IGHV4-39, IGHV3-21, IGHV3-9, IGKV3D-15, MIR562, IGHV1-69, IGHV4-31, IGHV1-3, and OR2J3, but is not limited thereto.

In the present disclosure, the perfusion defect may be related to at least one gene selected from the group consisting of HLA-DQA1, AREG, SNHG29, and IGHV3-74, but is not limited thereto.

Still another aspect of the present disclosure is directed to a method for providing information needed for prediction of prognosis of a breast cancer patient, the method including:
 a phenotype determination step of determining a phenotype of a tumor by using an ultrasound image;
 a gene information determination step of determining at least one gene information related to breast cancer by using the phenotype of the tumor; and
 a prognosis prediction step of predicting a prognosis of a breast cancer patient through the determined gene information.

In the present disclosure, the ultrasound image may be at least one selected from the group consisting of a B-mode ultrasound image, a superb microvascular imaging (SMI) ultrasound image, and a contrast-enhanced ultrasound (CEUS) image, and may include, for example, a B-mode ultrasound image, an SMI ultrasound image, and a contrast-enhanced ultrasound image.

In the present disclosure, the phenotype determined through the B-mode ultrasound image may be at least one selected from the group consisting of size, shape, orientation, margin, and calcifications, and may include, for example, size, shape, orientation, margin, and calcifications.

In the present disclosure, the size may be related to at least one gene selected from the group consisting of MIR941-1, IGLV6-57, HIST1H1B, HIST1H3I, ADH1B, PLIN4, and LUZP6, but is not limited thereto.

In the present disclosure, the shape may be related to at least one gene selected from the group consisting of MIR941-1, ZFP36L1, SNHG9, H2AFY2, POTEI, UBE2Q2L, FABP7, IGHV3-43, IGKJ5, and IGKJ2, but is not limited thereto.

In the present disclosure, the orientation may be related to at least one gene selected from the group consisting of TFF1, AREG, AGR3, TFF3, LINC00993, IGKV2-28, IGLV1-51, IGHV3-73, IGKV3-20, IGLV2-14, IGKV1-12, IGHV4-61, IGKV3D-15, IGHV1-3, IGHV4-4, IGHV1-18, IGHV4-34, IGHV3-74, CALML5, IGHJ5, and IGKJ2, but is not limited thereto.

In the present disclosure, the margin may be related to HLA-C gene, but is not limited thereto.

In the present disclosure, the calcifications may be related to at least one gene selected from the group consisting of CALML3, HIST1H4F, IGHV4OR15-8, CCL19, and IGLV8-61, but is not limited thereto.

In the present disclosure, the phenotype determined through the SMI ultrasound image may be at least one selected from the group consisting of vascular index, vessel morphology, and penetrating vessel, and may include, for example, vessel morphology, and penetrating vessel.

In the present disclosure, the vascular index may be related to at least one gene selected from the group consisting of IGHJ5, MIR1307, IGLV6-57, HLA-C, HIST2H2BE, CALML3, IGKV6-21, OR5P3, and MIR597, but is not limited thereto.

In the present disclosure, the vessel morphology may be related to at least one gene selected from the group consisting of HIST1H4D, TUSC1, FZD8, NMI, IGF1R, UBB, SERHL2, NFIL3, CRIPAK, SNHG20, HBA2, and SNHG12, but is not limited thereto.

In the present disclosure, the penetrating vessel may be related to at least one gene selected from the group consisting of HIST1H4D, CST1, TRBC2, SLC25A2, KRT14, MFAP4, IGKV2-40, NFIL3, POTEE, POTEI, ALDH3B2, CRIPAK, IGHJ2, AREG, and IGKJ5, but is not limited thereto.

In the present disclosure, the phenotype determined through the contrast-enhanced ultrasound image may be at least one selected from the group consisting of enhancement order, enhancement margin, internal homogeneity, penetrating vessel, and perfusion defect, and may include, for example, enhancement order, enhancement margin, internal homogeneity, penetrating vessel, and perfusion defect.

In the present disclosure, the enhancement order may be related to at least one gene selected from the group consisting of IGKV1D-39, CCL3L3, IGHG4, IGKV1D-12, IGKV3D-11, SNHG12, CPB1, MIR562, and VTRNA2-1, but is not limited thereto.

In the present disclosure, the enhancement margin may be related to at least one gene selected from the group consisting of STH, TFF1, STC2, AMY2A, HOXB5, IGKV1D-39, PHLDA2, HIST1H2AJ, TRAV14DV4, HIST1H1A, CXCL10, ISG15, IGHV4-39, IGKV3D-15, HIST2H2BF, HIST1H2BM, IGKV2-28, IGHV3-21, CALML5, IGHV1-18, IGKV2-29, IGHG4, IGHJ4, IGHJ5, and IGKJ2, but is not limited thereto.

In the present disclosure, the internal homogeneity may be related to at least one gene selected from the group consisting of IGKJ5, HLA-DQA1, HIST1H1B, and IGHV3-74, but is not limited thereto.

In the present disclosure, the penetrating vessel may be related to at least one gene selected from the group consisting of AGR2, HIST1H2BI, IGHV4-4, IGLV3-25, IGKV1D-39, IGHV1-2, IGHV3-15, IGKV1-27, IGLV3-1, IGKV2-40, IGKV2D-40, IGHV1-18, HIST1H2AG, IGHV3-33, IGKV1-12, IGKV1-17, IGHG1, TRBV5-6, IGHG4, IGHV4-61, IGKV2-28, IGHV1-8, IGHV4-39, IGHV3-21, IGHV3-9, IGKV3D-15, MIR562, IGHV1-69, IGHV4-31, IGHV1-3, and OR2J3, but is not limited thereto.

In the present disclosure, the perfusion defect may be related to at least one gene selected from the group consisting of HLA-DQA1, AREG, SNHG29, and IGHV3-74, but is not limited thereto.

Still another aspect of the present disclosure is directed to a method for providing information for choosing a breast cancer therapy by using an ultrasound image of breast cancer and performing a therapy, the method including:

a phenotype determination step of determining a phenotype of a tumor by using an ultrasound image;

a gene information determination step of determining at least one gene information related to breast cancer by using the phenotype of the tumor;

a therapy determination step of determining an individual breast cancer therapy by correlating the determined genetic information with genetic information associated with a breast cancer therapy; and a step of treating a subject by using the determined therapy.

The step of treating the subject may be performed by surgery therapy, chemotherapy, radiation therapy, hormone therapy, photodynamic therapy, laser therapy, immunotherapy, gene therapy, or the like, but is not limited thereto.

As used herein, the term "subject (individual)" refers to a mammal including a human, a mouse, a rat, a guinea pig, a dog, a cat, a horse, a cow, a pig, a monkey, a chimpanzee, a baboon, a rhesus monkey, and the like. Most specifically, the subject of the present disclosure is a human.

Since the method for information provision and treatment of the present disclosure overlaps the method for providing information for choosing a breast cancer therapy according to an aspect of the present disclosure in terms of a phenotype determination step, a gene information determination step, and a therapy determination step, a description of overlapping contents therebetween is omitted to avoid excessive redundancy of the present specification.

Advantageous Effects of Invention

The present disclosure relates to a method for providing information for choosing a breast cancer therapy by using an ultrasound image of breast cancer and gene information, a system for choosing a breast cancer therapy by using an ultrasound image of breast cancer, and a method for providing information needed for prediction of prognosis of a breast cancer patient.

BRIEF DESCRIPTION OF THE DRAWINGS

In FIG. 3A, the top network with a score of 29 including TFF1, TFF3, TP53, TGFBR2, AR, BAX, TERT, and POUF51 was associated with cell cycle, cellular growth and proliferation, and cancer. TFF1 and TFF3 were significantly upregulated genes showing direct interactions with TP53 and AR, respectively In FIG. 3B, the second highest scoring network with a score of 21, including CCND1, AREG, NFKB1, CTNNB1, and RAC1, was associated with cancer, organismal survival, and injury.

DETAILED DESCRIPTION

Figure 1A:
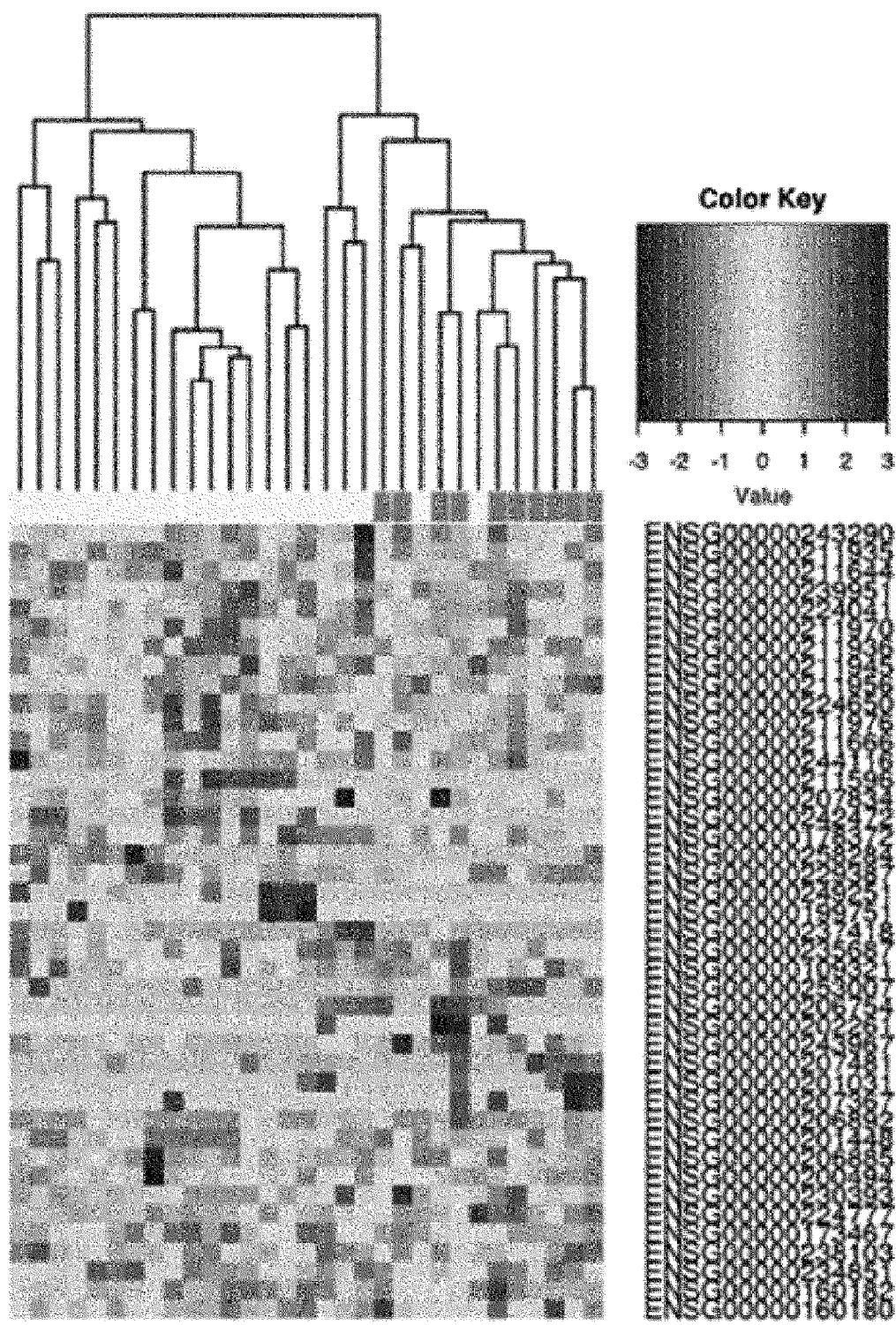
FIG. 1A is a heat map image showing radiogenomic correlations according to the orientation at B-mode ultrasound imaging in 31 patients with breast cancer according to an example of the present disclosure. The heat map image shows 42 differentially expressed genes of log 2fc>2 or <−2. The rows represent individual tissue samples and the columns represent individual gene signature (Ensemble gene ID).
Figure 1B:
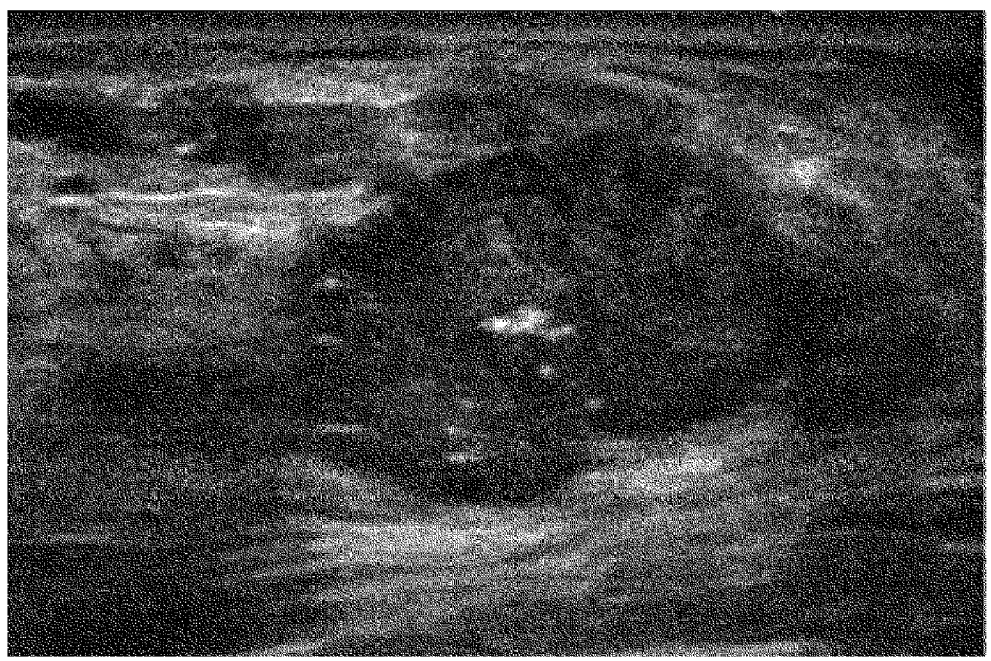
FIG. 1B is an ultrasound image showing cancer with parallel orientation in a 53-year-old patient according to an example of the present disclosure.
Figure 1C:
FIG. 1C is an ultrasound image showing cancer with non-parallel orientation in a 48-year-old patient according to an example of the present disclosure.
Figure 1D:
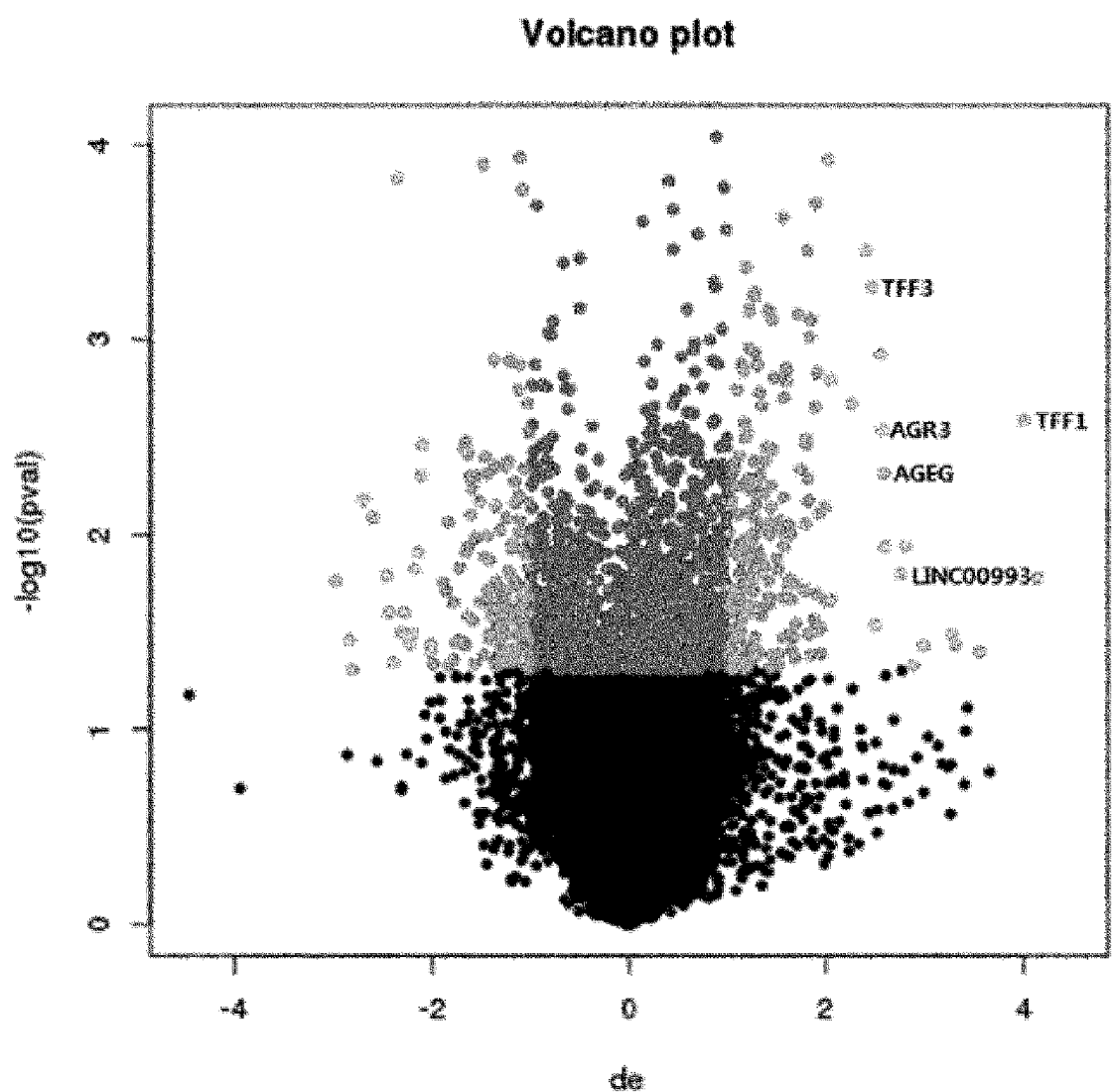
FIG. 1D is a volcano plot image showing radiogenomic correlations according to the orientation at B-mode ultrasound imaging in 31 patients with breast cancer according to an example of the present disclosure.
Figure 2A:
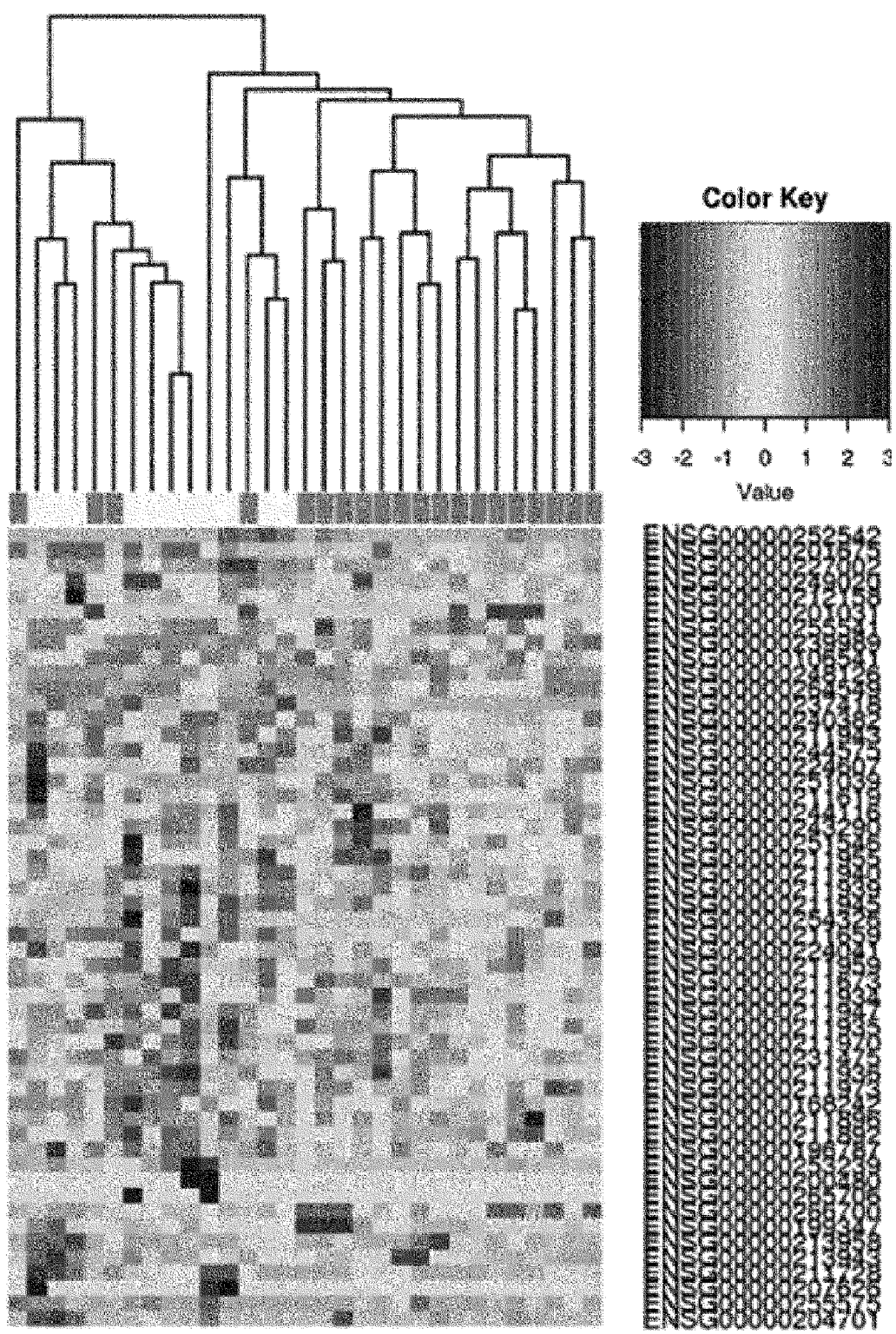
FIG. 2A is a heat map image showing radiogenomic correlations according to the presence of penetrating vessels at contrast agent-enhanced ultrasound in 31 patients with breast cancer according to an example of the present disclosure. The heat map image shows 52 differentially expressed genes of log 2fc>2 or <−2. The rows represent individual tissue samples and the columns represent individual gene signature (Ensemble green ID).
Figure 2B:
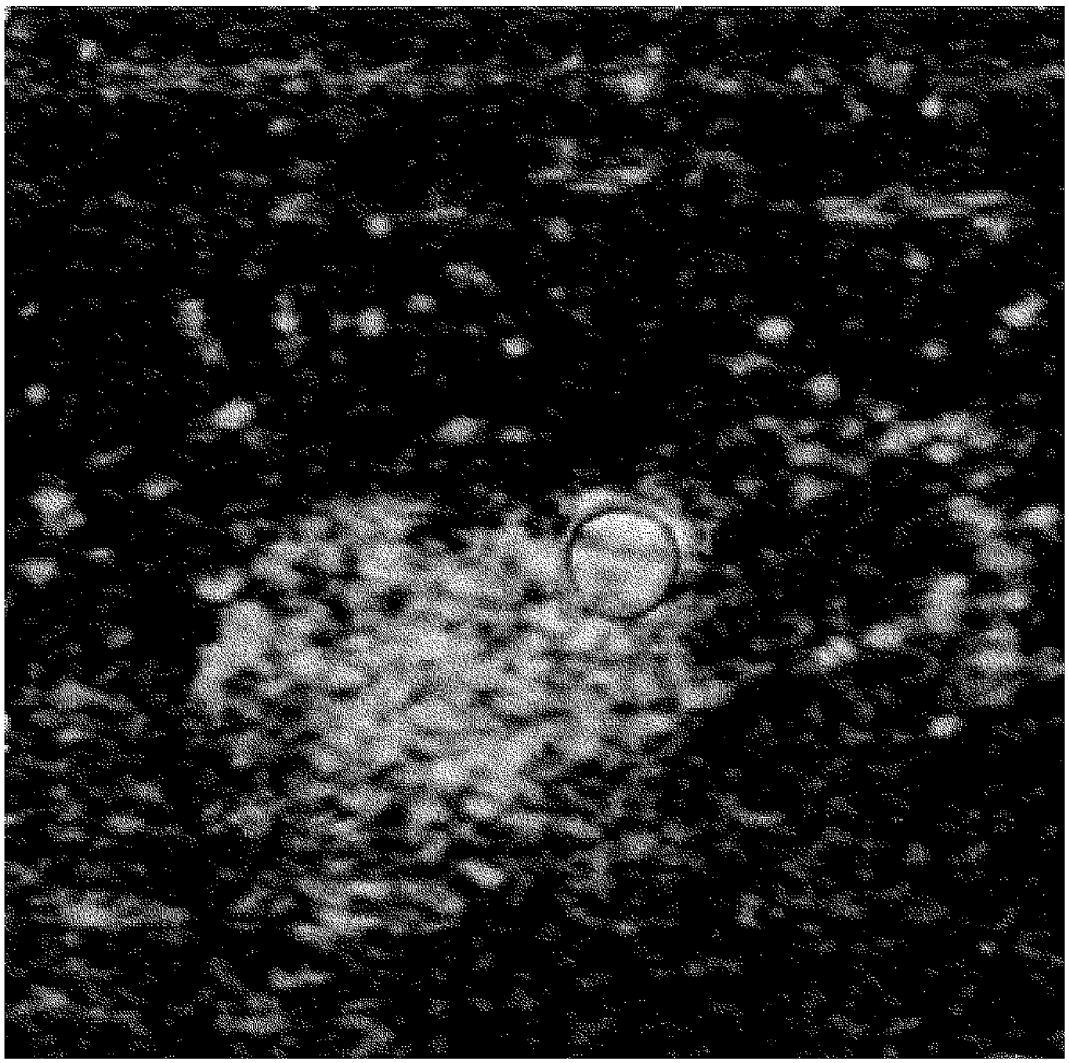
FIG. 2B is an ultrasound image showing cancer without penetrating vessel in a 50-year-old patient according to an example of the present disclosure.
Figure 2C:
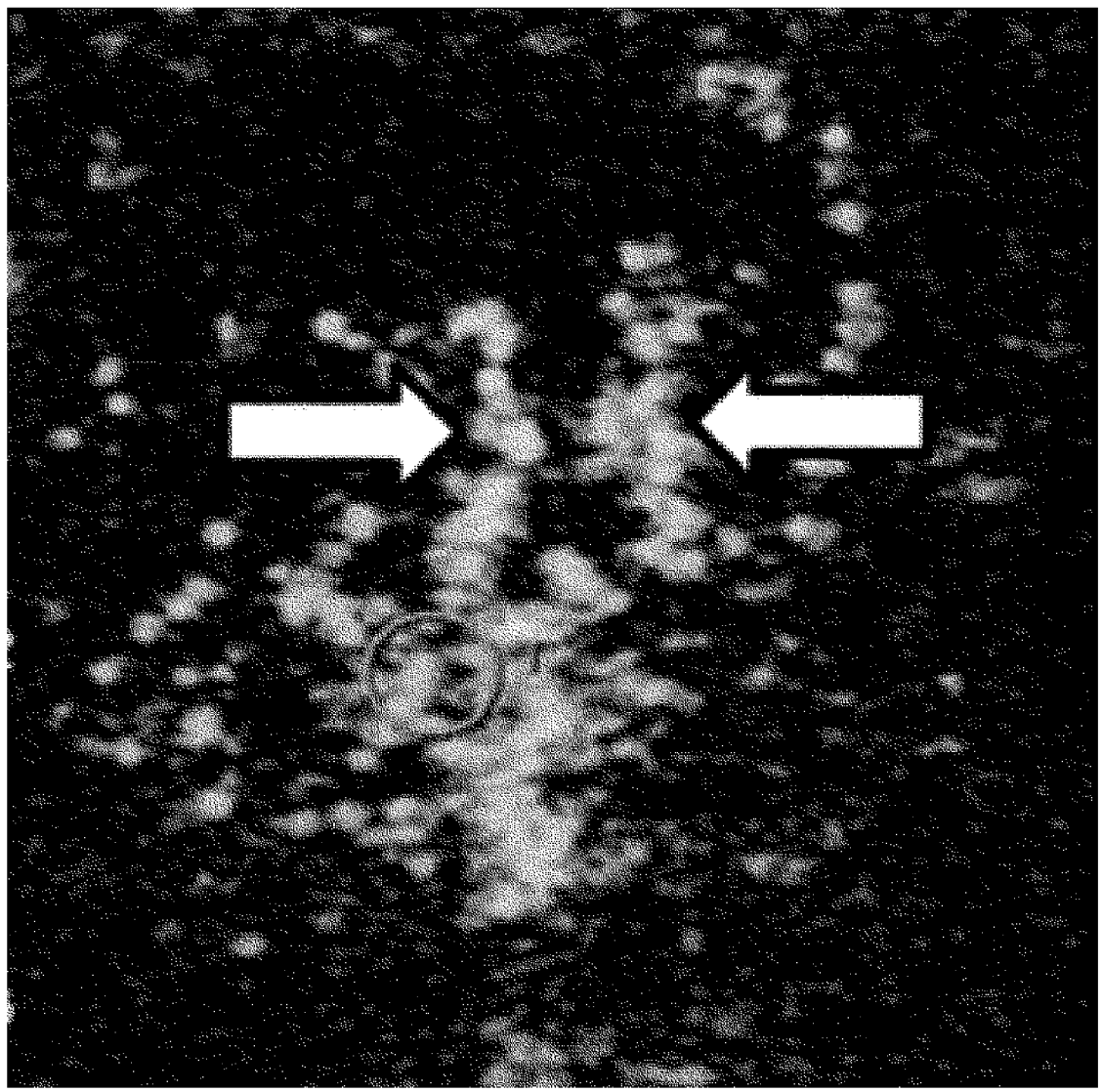
FIG. 2C is an ultrasound image showing cancer with penetrating vessel in a 74-year-old patient according to an example of the present disclosure.
Figure 2D:
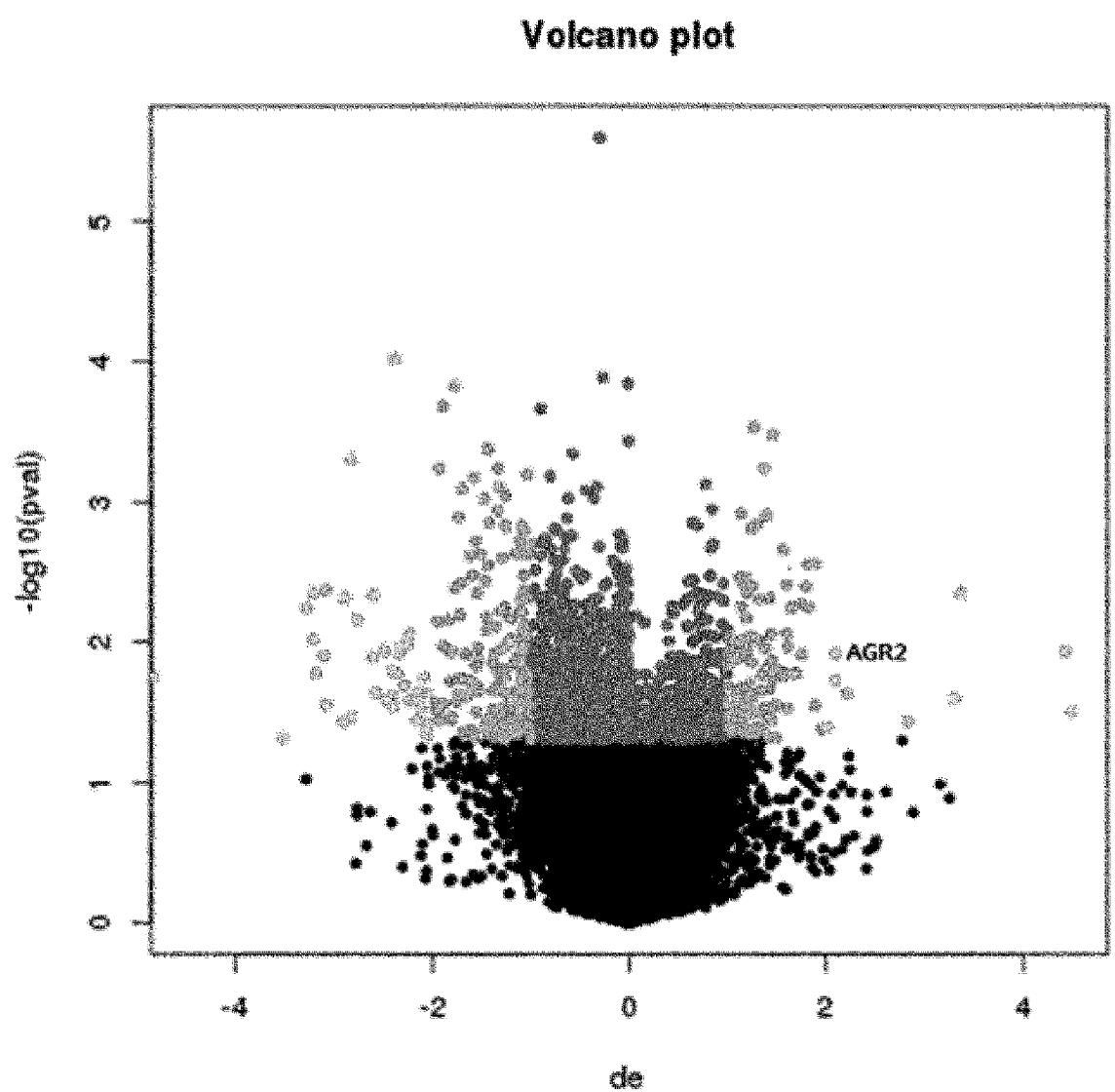
FIG. 2D is a volcano plot image showing radiogenomic correlations according to the presence of penetrating vessels at contrast agent-enhanced ultrasound imaging in 31 patients with breast cancer according to an example of the present disclosure.

Hereinafter, the present disclosure will be described in more detail by the following examples. However, these examples are used only for illustration, and the scope of the present disclosure is not limited by these examples.

Example 1: Patient Characteristics

This study was approved by the institutional review board. From January to October 2016, breast tumor patients (57 benign and 41 malignant) were included in a preliminary prospective study to assess association values between ultrasound parameters and histologic microvessel densities at vascular ultrasound imaging (SMI and CEUS) in the distinguishment of malignant from benign tumors. Of the 41 patients with malignant breast cancer, 31 patients (mean: 49.4 years old, range: 36-76 years old) who signed written informed consent to gene sequencing were included in the present study for correlation with vascular ultrasound imaging (SMI and CEUS) features of breast cancer. For 31 breast cancers (mean size: 21.8 mm, range: 7-48 mm), B-mode and vascular ultrasound (SMI and CEUS) images were observed. NGS was performed by using the whole genomic RNA obtained from surgically incised breast cancer tissues. Patient characteristics were summarized and shown in Table 1 below.

TABLE 1

| Index | — | Number (percentage) |
|---|---|---|
| B-mode ultrasound | — | — |
| Size | <20 mm | 17 (54.8) |
|  | ≥20 mm | 14 (45.2) |
| Shape | Oval | 5 (16.1) |
|  | Irregular | 26 (83.9) |
| Echo pattern | Isoechoic | 3 (9.7) |
|  | Heterogeneous | 2 (6.5) |
|  | Complex cystic and solid | 1 (3.2) |
|  | Hypoechoic | 25 (80.6) |
| Orientation | Parallel | 21 (67.7) |
|  | Not parallel | 10 (32.3) |
| Margin | Indistinct | 13 (41.9) |
|  | Angular | 6 (19.4) |
|  | Microlobulated | 7 (22.6) |
|  | Spiculated | 5 (16.1) |
| Calcifications | Absent | 18 (58.1) |
|  | Present | 13 (41.9) |
| Superb microvascular imaging |  |  |
| Vascular index | <16.1% | 19 (61.3) |
|  | ≥16.1% | 12 (38.7) |
| Vessel morphology | None or simple | 6 (19.4) |
|  | Complex | 25 (80.6) |
| Vessel distribution | None or peripheral | 2 (6.5) |
|  | Central | 29 (93.5) |
| Penetrating vessel | Absent | 6 (19.4) |
|  | Present | 25 (80.6) |
| Contrast-enhanced ultrasound |  |  |
| Enhancement degree | Hypo-enhancement | 1 (3.2) |
|  | Iso-enhancement | 1 (3.2) |
|  | Hyper-enhancement | 29 (93.6) |
| Enhancement order | Diffuse | 9 (29.0) |
|  | Centripetal | 22 (71.0) |
| Enhancement margin | Circumscribed | 13 (41.9) |
|  | Not circumscribed | 18 (58.1) |
| Internal homogeneity | Homogeneous | 17 (54.8) |
|  | Heterogeneous | 14 (45.2) |
| Penetrating vessel | Absent | 11 (35.5) |
|  | Present | 20 (64.5) |
| Perfusion defect | Absent | 20 (64.5) |
|  | Present | 11 (35.5) |
| Pathology |  |  |
| Tumor type | Invasive ductal carcinoma | 27 (87.1) |
|  | Ductal carcinoma in situ | 4 (12.9) |
| Immunohistochemical result | ER positive | 21/31 (67.7) |
|  | PR positive | 22/31 (71.0) |
|  | HER2 positive | 8/31 (25.8) |

ER = estrogen receptor, PR = progesterone receptor, HER2 = human epidermal growth factor receptor 2

In 16 ultrasound imaging phenotypes, the analyses for echo pattern at B-mode ultrasound, vessel distribution at SMI, and enhancement order at contrast-enhanced ultrasound were excluded since the numbers of samples of two groups were not balanced and data were skewed to one group between the two to result in low statistical reliability.

Example 2: Ultrasound Imaging and Analyses

Aplio 500 system (Canon Medical Systems, Tokyo, Japan) with a 5-14 MHz linear transducer was used. The ultrasound examinations were performed by a radiologist with 18 years of experience in breast examinations. Two radiologists (with 12 and 5 years of experience in breast imaging, respectively) analyzed the imaging phenotypes according to breast imaging reports and data systems: B-mode phenotypes included size (20 mm vs<20 mm), shape (irregular vs oval or round), echo pattern (complex cystic and solid or hypoechoic vs isoechoic or heterogeneous), orientation (not parallel vs parallel), margin (angular, microlobulated, or spiculated vs indistinct), and calcifications (present vs absent).

After B-mode ultrasound evaluation, SMI and CEUS were performed. At SMI, the plane with the richest vessels was stored as a representative image for evaluation. CEUS was performed immediately after SMI. The contrast agent (SonoVue (Bracco, Milan, Italy)) was mixed with saline and injected in a bolus fashion, and video clips were recorded during continuous scanning. The imaging parameters for SMI were velocity scale<3 cm/s, dynamic range 21 dB, and frame rate 27-60 frames/s. Those for CEUS were mechanical index 0.08, frame rate 10 frames/s, gain 80, and dynamic range 65 dB.

The SMI phenotypes included vascular index (%, the ratio between the pixels for the Doppler signal and those for the whole lesion, the mean vascular index of <31 cancers vs mean vascular index), vessel morphology (complex (branching or shunting) vs none or simple (dot-like or linear)), distribution (central (vessel detected within the lesion) vs none or peripheral (all vessels located at the margin)), and penetrating vessels (present vs absent).

The CEUS phenotypes included enhancement degree (hyperenhancement vs iso- or hypoenhancement), order (centripetal vs centrifugal or diffuse), margin (uncircumscribed vs circumscribed), internal homogeneity (heterogeneous vs homogeneous), penetrating vessels (present vs absent), and perfusion detection (present vs absent).

Example 3: RNA Sequencing and Analyses

Total RNA concentration was calculated by using Quant-IT RiboGreen (Invitrogen, USA) and 100 ng was subjected to sequencing library construction. The mRNA-seq library was prepared using the paired-end mRNA sequencing sample preparation kit (TruSeq RNA access library kit, Illumina, USA). By using the Illumina HiSeq 2500 sequencing system, paired-end sequencing (2×100 bp) was performed. Low-quality and adapter sequences from produced paired-end reads were trimmed using the Trim Galore software (version 0.5.0) and Cutadapt (version 1.18).

The genome analysis toolkit, which was the best practice for workflow for SNP and InDel calling on RNA sequencing data, was used. Briefly, the spliced transcripts alignment to a reference 2-pass method was used to align trimmed reads to the human reference genome (hg19). Picard command line tools were used to process SAM files produced in the above-mentioned step to add read group information, sorting, marking duplicates, and indexing. Variants were called and filtered using the genome analysis toolkit tools HaplotypeCaller and VariantFiltration. RNA variants were annotated using ANNOVAR. Functional enrichment analysis and pathway analysis were performed by using ingenuity pathway analysis software (Ingenuity Systems, USA).

Example 4: Correlations Between Ultrasound Imaging Phenotypes and Gene Expressions The genes expressed differentially between two groups of each ultrasound imaging phenotype were detected by using Tablemaker and Ballgown. First, Tablemaker (version 2.1.1) was used to estimate fragments per kilobase of transcript per million mapped reads (FPKM) for each assembled transcript. Then, the results from Tablemaker were integrated into the software environment R (version 3.5.0) by using the R package Ballgown (version 2.10.0). Ballgown was used to calculate differential gene expression from RNA sequencing data. FPKM was used to estimate the level of gene expression, and the P value for differential expression was extracted by using a parametric F-test comparing nested linear models. The log 2 fold change (log 2fc) of the gene expression between two groups was calculated by using the Ballgown "stattest" function. Differential gene expression results were visualized by using a volcano plot and heat map in R. The results are shown in FIGS. 1 and 2.

Conclusion

Genes Expressed Differentially According to Ultrasound Imaging Phenotypes

A total of 340 genes were expressed differentially according to the ultrasound imaging phenotypes with the standard of $P<0.05$ and log 2fc>2 or <−2: 92 genes were upregulated and 263 were downregulated. Of these, 228 were noncoding RNA with unknown function or pseudogenes, and the other 112 were protein-coding genes (n=102) or noncoding RNA with known function (microRNA (n=5), snoRNA (n=4), and lncRNA (n=1)).

Tables 2 to 14 show the summary of 112 significantly up- or down-regulated genes according to ultrasound imaging phenotypes. Twenty-seven of the 112 genes have been reported as being relevant to breast cancer in terms of tumor growth, invasion, metastasis, and drug resistance. (*: genes reported as being relevant to breast cancer)

TABLE 2

| Gene Symbol | Gene Name | Log2fc | P Value |
| --- | --- | --- | --- |
| MIR941-1 | MicroRNA 941-1 | 4.04 | <0.01 |
| IGLV6-57 | Immunoglobulin Lambda Variable 6-57 | 2.44 | 0.02 |
| HIST1H1B | Histone Cluster 1 H1 Family Member B | 2.05 | 0.03 |
| HIST1H3I | Histone Cluster 1 H3 Family Member I | 2.01 | 0.01 |
| ADH1B | Alcohol Dehydrogenase 1B (Class I), Beta Polypeptide | −2.24 | <0.01 |
| PLIN4 | Perilipin 4 | −2.40 | 0.01 |
| LUZP6 | Leucine Zipper Protein 6 | −3.15 | 0.02 |

Genes expressed differentially according to ultrasound imaging phenotype—B-mode ultrasound_Size

TABLE 3

| Gene Symbol | Gene Name | Log2fc | P Value |
| --- | --- | --- | --- |
| MIR941-1 | MicroRNA 941-1 | 4.64 | 0.01 |
| ZFP36L1* | ZFP36 Ring Finger Protein Like 1 | 2.08 | <0.01 |
| SNHG9 | Small Nucleolar RNA Host Gene 9 | 2.00 | 0.02 |

TABLE 3-continued

| Gene Symbol | Gene Name | Log2fc | P Value |
|---|---|---|---|
| H2AFY2 | H2A Histone Family Member Y2 | −2.03 | <0.01 |
| POTEI | POTE Ankyrin Domain Family Member I | −2.10 | 0.01 |
| UBE2Q2L | Ubiquitin Conjugating Enzyme E2 Q2 Like | −2.13 | 0.04 |
| FABP7* | Fatty Acid Binding Protein 7 | −2.36 | 0.01 |
| IGHV3-43 | Immunoglobulin Heavy Variable 3-43 | −2.76 | 0.05 |
| IGKJ5 | Immunoglobulin Kappa Joining 5 | −7.82 | 0.01 |
| IGKJ2 | Immunoglobulin Kappa Joining 2 | −9.27 | 0.03 |

Genes expressed differentially according to ultrasound imaging phenotype—B-mode ultrasound_Shape

TABLE 4

| Gene Symbol | Gene Name | Log2fc | P Value |
|---|---|---|---|
| TFF1* | Trefoil Factor 1 | 4.00 | <0.01 |
| AREG* | Amphiregulin | 2.58 | <0.01 |
| AGR3* | Anterior Gradient 3, Protein Disulphide Isomerase Family Member | 2.57 | <0.01 |
| TFF3* | Trefoil Factor 3 | 2.47 | <0.01 |
| LINC00993* | Long Intergenic Non-Protein Coding RNA 993 | 2.05 | 0.02 |
| IGKV2-28 | Immunoglobulin Kappa Variable 2-28 | −2.01 | 0.04 |
| IGLV1-51 | Immunoglobulin Lambda Variable 1-51 | −2.02 | 0.04 |
| IGHV3-73 | Immunoglobulin Heavy Variable 3-73 | −2.10 | <0.01 |
| IGKV3-20 | Immunoglobulin Kappa Variable 3-20 | −2.18 | 0.02 |
| IGLV2-14 | Immunoglobulin Lambda Variable 2-14 | −2.20 | 0.03 |
| IGKV1-12 | Immunoglobulin Kappa Variable 1-12 | −2.25 | 0.03 |
| IGHV4-61 | Immunoglobulin Heavy Variable 4-61 | −2.28 | 0.03 |
| IGKV3D-15 | Immunoglobulin Kappa Variable 3D-15 | −2.31 | 0.03 |
| IGHV1-3 | Immunoglobulin Heavy Variable 1-3 | −2.40 | 0.05 |
| IGHV4-4 | Immunoglobulin Heavy Variable 4-4 | −2.44 | 0.03 |
| IGHV1-18 | Immunoglobulin Heavy Variable 1-18 | −2.46 | 0.02 |
| IGHV4-34 | Immunoglobulin Heavy Variable 4-34 | −2.60 | 0.01 |
| IGHV3-74 | Immunoglobulin Heavy Variable 3-74 | −2.70 | 0.01 |
| CALML5 | Calmodulin Like 5 | −2.98 | 0.02 |
| IGHJ5 | Immunoglobulin Heavy Joining 5 | −5.60 | 0.03 |
| IGKJ2 | Immunoglobulin Kappa Joining 2 | −7.12 | 0.05 |

Genes expressed differentially according to ultrasound imaging phenotype—B-mode ultrasound_Orientation

TABLE 5

| Gene Symbol | Gene Name | Log2fc | P Value |
|---|---|---|---|
| HLA-C | Major Histocompatibility Complex, Class I, C | 2.13 | 0.01 |

Genes expressed differentially according to ultrasound imaging phenotype—B-mode ultrasound_Margin

TABLE 6

| Gene Symbol | Gene Name | Log2fc | P Value |
|---|---|---|---|
| CALML3 | Calmodulin Like 3 | −2.03 | 0.02 |
| HIST1H4F | Histone Cluster 1 H4 Family Member F | −2.03 | 0.01 |
| IGHV4OR15-8 | Immunoglobulin Heavy Variable 4/OR15-8 | −2.05 | 0.02 |
| CCL19 | C-C motif chemokine ligand 19 | −2.19 | 0.01 |
| IGLV8-61 | Immunoglobulin Lambda Variable 8-61 | −2.53 | 0.03 |

Genes expressed differentially according to ultrasound imaging phenotype—B-mode ultrasound_Calcifications

TABLE 7

| Gene Symbol | Gene Name | Log2fc | P Value |
|---|---|---|---|
| IGHJ5 | Immunoglobulin Heavy Joining 5 | 5.80 | 0.02 |
| MIR1307* | MicroRNA 1307 | 3.53 | <0.01 |
| IGLV6-57 | Immunoglobulin Lambda Variable 6-57 | 2.49 | 0.01 |
| HLA-C | Major Histocompatibility Complex, Class I, C | 2.21 | 0.01 |
| HIST2H2BE* | Histone Cluster 2 H2B Family Member E | 2.05 | <0.01 |
| CALML3 | Calmodulin Like 3 | −2.25 | <0.01 |
| IGKV6-21 | Immunoglobulin Kappa Variable 6-21 | −2.37 | 0.02 |
| OR5P3 | Olfactory Receptor Family 5 Subfamily P Member 3 | −2.37 | <0.01 |
| MIR597* | MicroRNA 597 | −2.64 | 0.05 |

Genes expressed differentially according to ultrasound imaging phenotype—SMI_Vascular index

TABLE 8

| Gene Symbol | Gene Name | Log2fc | P Value |
|---|---|---|---|
| HIST1H4D | Histone Cluster 1 H4 Family Member D | 2.68 | 0.01 |
| TUSC1 | Tumor Suppressor Candidate 1 | 2.55 | <0.01 |
| FZD8* | Frizzled Class Receptor 8 | 2.02 | 0.01 |
| NMI* | N-Myc And STAT Interactor | −2.02 | <0.01 |
| IGF1R* | Insulin Like Growth Factor 1 Receptor | −2.03 | 0.01 |
| UBB* | Ubiquitin B | −2.05 | 0.01 |
| SERHL2 | Serine Hydrolase Like 2 | −2.06 | 0.03 |
| NFIL3 | Nuclear Factor, Interleukin 3 Regulated | −2.12 | <0.01 |
| CRIPAK* | Cysteine Rich PAK1 Inhibitor | −2.42 | 0.01 |
| SNHG20* | Small Nucleolar RNA Host Gene 20 | −2.42 | 0.04 |
| HBA2 | Hemoglobin Subunit Alpha 2 | −2.57 | 0.05 |
| SNHG12* | Small Nucleolar RNA Host Gene 12 | −3.11 | 0.01 |

Genes expressed differentially according to ultrasound imaging phenotype—SMI_Vessel morphology

TABLE 9

| Gene Symbol | Gene Name | Log2fc | P Value |
|---|---|---|---|
| HIST1H4D | Histone Cluster 1 H4 Family Member D | 3.45 | <0.01 |
| CST1* | Cystatin SN | 2.65 | <0.01 |
| TRBC2 | T Cell Receptor Beta Constant 2 | 2.22 | 0.01 |
| SLC25A2 | Solute Carrier Family 25 Member 2 | −2.00 | 0.01 |
| KRT14 | Keratin 14 | −2.02 | 0.02 |
| MFAP4 | Microfibril Associated Protein 4 | −2.06 | <0.01 |
| IGKV2-40 | Immunoglobulin Kappa Variable 2-40 | −2.07 | 0.05 |
| NFIL3 | Nuclear Factor, Interleukin 3 Regulated | −2.12 | 0.01 |
| POTEE | POTE Ankyrin Domain Family Member E | −2.35 | 0.02 |
| POTEI | POTE Ankyrin Domain Family Member I | −2.39 | <0.01 |
| ALDH3B2 | Aldehyde Dehydrogenase 3 Family Member B2 | −2.40 | 0.01 |
| CRIPAK* | Cysteine Rich PAK1 Inhibitor | −2.57 | 0.01 |
| IGHJ2 | Immunoglobulin Heavy Joining 2 | −3.01 | 0.04 |
| AREG* | Amphiregulin | −3.03 | 0.01 |
| IGKJ5 | Immunoglobulin Kappa Variable 1D-39 | −6.58 | 0.02 |

Genes expressed differentially according to ultrasound imaging phenotype—SMI_Penetrating vessel

TABLE 10

| Gene Symbol | Gene Name | Log2fc | P Value |
| --- | --- | --- | --- |
| IGKV1D-39 | Immunoglobulin Kappa Variable 1D-39 | −2.01 | 0.03 |
| CCL3L3 | C-C Motif Chemokine Ligand 3 Like 3 | −2.06 | 0.03 |
| IGHG4 | Immunoglobulin Heavy Constant Gamma 4 (G4m Marker) | −2.08 | 0.03 |
| IGKV1D-12 | Immunoglobulin Kappa Variable 1D-12 | −2.15 | 0.03 |
| IGKV3D-11 | Immunoglobulin Kappa Variable 3D-11 | −2.25 | 0.02 |
| SNHG12* | Small Nucleolar RNA Host Gene 12 | −2.54 | <0.01 |
| CPB1 | Carboxypeptidase B1 | −2.71 | <0.01 |
| MIR562* | MicroRNA 562 | −3.19 | <0.01 |
| VTRNA2-1* | Vault RNA 2-1 | −5.85 | 0.01 |

Genes expressed differentially according to ultrasound imaging phenotype—Contrast-enhanced ultrasound_Enhancement order

TABLE 11

| Gene Symbol | Gene Name | Log2fc | P Value |
| --- | --- | --- | --- |
| STH | Saitohin | 3.12 | <0.01 |
| TFF1* | Trefoil Factor 1 | 2.95 | 0.02 |
| STC2* | Stanniocalcin 2 | 2.66 | <0.01 |
| AMY2A | Amylase, Alpha 2A (Pancreatic) | 2.28 | <0.01 |
| HOXB5* | Homeobox B5 | 2.17 | <0.01 |
| IGKV1D-39 | Immunoglobulin Kappa Variable 1D-39 | −2.01 | 0.02 |
| PHLDA2* | Pleckstrin Homology Like Domain Family A Member 2 | −2.01 | <0.01 |
| HIST1H2AJ | Histone Cluster 1 H2A Family Member J | −2.04 | 0.03 |
| TRAV14DV4 | T Cell Receptor Alpha Variable 14/Delta Variable 4 | −2.06 | <0.01 |
| HIST1H1A | Histone Cluster 1 H1 Family Member A | −2.08 | 0.01 |
| CXCL10* | C-X-C Motif Chemokine Ligand 10 | −2.08 | 0.01 |
| ISG15 | ISG15 Ubiquitin-Like Modifier | −2.16 | 0.01 |
| IGHV4-39 | Immunoglobulin Heavy Variable 4-39 | −2.19 | 0.02 |
| IGKV3D-15 | Immunoglobulin Kappa Variable 3D-15 | −2.25 | 0.03 |
| HIST2H2BF | Histone Cluster 2 H2B Family Member F | −2.25 | 0.01 |
| HIST1H2BM | Histone Cluster 1 H2B Family Member M | −2.25 | 0.03 |
| IGKV2-28 | Immunoglobulin Kappa Variable 2-28 | −2.29 | 0.02 |
| IGHV3-21 | Immunoglobulin Heavy Variable 3-21 | −2.52 | 0.02 |
| CALML5 | Calmodulin Like 5 | −2.66 | 0.03 |
| IGHV1-18 | Immunoglobulin Heavy Variable 1-18 | −2.79 | 0.01 |
| IGKV2-29 | Immunoglobulin Kappa Variable 2-29 | −2.83 | <0.01 |
| IGHG4 | Immunoglobulin Heavy Constant Gamma 4 (G4m Marker) | −2.89 | 0.01 |
| IGHJ4 | Immunoglobulin Heavy Joining 4 | −6.92 | 0.02 |
| IGHJ5 | Immunoglobulin Heavy Joining 5 | −7.60 | <0.01 |
| IGKJ2 | Immunoglobulin Kappa Joining 2 | −8.61 | 0.01 |

Genes expressed differentially according to ultrasound imaging phenotype—Contrast-enhanced ultrasound_Enhancement margin

TABLE 12

| Gene Symbol | Gene Name | Log2fc | P Value |
| --- | --- | --- | --- |
| IGKJ5 | Immunoglobulin Kappa Joining 5 | 4.65 | 0.05 |
| HLA-DQA1* | Major Histocompatibility Complex, Class II, DQ Alpha 1 | 3.29 | <0.01 |
| HIST1H1B | Histone Cluster 1 H1 Family Member B | 2.02 | 0.05 |
| IGHV3-74 | Immunoglobulin Heavy Variable 3-74 | −2.37 | 0.01 |

Genes expressed differentially according to ultrasound imaging phenotype—Contrast-enhanced ultrasound_Internal homogeneity

TABLE 13

| Gene Symbol | Gene Name | Log2fc | P Value |
| --- | --- | --- | --- |
| AGR2* | Anterior Gradient 2, Protein Disulphide Isomerase Family Member | 2.09 | 0.01 |
| HIST1H2BI | Histone Cluster 1 H2B Family Member I | −2.05 | 0.02 |
| IGHV4-4 | Immunoglobulin Heavy Variable 4-4 | −2.05 | 0.05 |
| IGLV3-25 | Immunoglobulin Lambda Variable 3-25 | −2.06 | 0.04 |
| IGKV1D-39 | Immunoglobulin Kappa Variable 1D-39 | −2.09 | 0.02 |
| IGHV1-2 | Immunoglobulin Heavy Variable 1-2 | −2.12 | 0.03 |
| IGHV3-15 | Immunoglobulin Heavy Variable 3-15 | −2.13 | 0.03 |
| IGKV1-27 | Immunoglobulin Kappa Variable 1-27 | −2.13 | 0.03 |
| IGLV3-1 | Immunoglobulin Lambda Variable 3-1 | −2.15 | 0.03 |
| IGKV2-40 | Immunoglobulin Kappa Variable 2-40 | −2.16 | 0.04 |
| IGKV2D-40 | Immunoglobulin Kappa Variable 2D-40 | −2.23 | 0.01 |
| IGHV1-18 | Immunoglobulin Heavy Variable 1-18 | −2.23 | 0.01 |
| HIST1H2AG | Histone Cluster 1 H2A Family Member G | −2.26 | 0.01 |
| IGHV3-33 | Immunoglobulin Heavy Variable 3-33 | −2.29 | 0.02 |
| IGKV1-12 | Immunoglobulin Kappa Variable 1-12 | −2.34 | 0.01 |
| IGKV1-17 | Immunoglobulin Kappa Variable 1-17 | −2.34 | 0.01 |
| IGHG1 | Immunoglobulin Heavy Constant Gamma 1 (G1m Marker) | −2.36 | 0.02 |
| TRBV5-6 | T Cell Receptor Beta Variable 5-6 | −2.39 | <0.01 |
| IGHG4 | Immunoglobulin Heavy Constant Gamma 4 (G4m Marker) | −2.40 | 0.02 |
| IGHV4-61 | Immunoglobulin Heavy Variable 4-61 | −2.41 | 0.03 |
| IGKV2-28 | Immunoglobulin Kappa Variable 2-28 | −2.41 | 0.02 |
| IGHV1-8 | Immunoglobulin Heavy Variable 1-8 | −2.47 | 0.03 |
| IGHV4-39 | Immunoglobulin Heavy Variable 4-39 | −2.48 | 0.01 |
| IGHV3-21 | Immunoglobulin Heavy Variable 3-21 | −2.61 | 0.01 |
| IGHV3-9 | Immunoglobulin Heavy Variable 3-9 | −2.91 | 0.04 |
| IGKV3D-15 | Immunoglobulin Kappa Variable 3D-15 | −3.09 | <0.01 |
| MIR562* | MicroRNA 562 | −3.11 | 0.01 |
| IGHV1-69 | Immunoglobulin Heavy Variable 1-69 | −3.21 | 0.01 |
| IGHV4-31 | Immunoglobulin Heavy Variable 4-31 | −3.21 | <0.01 |
| IGHV1-3 | Immunoglobulin Heavy Variable 1-3 | −3.28 | 0.01 |
| OR2J3 | Olfactory Receptor Family 2 Subfamily J Member 3 | −3.52 | 0.05 |

Genes expressed differentially according to ultrasound imaging phenotype—Contrast-enhanced ultrasound_Penetrating vessel

TABLE 14

| Gene Symbol | Gene Name | Log2fc | P Value |
| --- | --- | --- | --- |
| HLA-DQA1* | Major Histocompatibility Complex, Class II, DQ Alpha 1 | 2.80 | <0.01 |
| AREG* | Amphiregulin | −2.02 | 0.02 |
| SNHG29 | Small Nucleolar RNA Host Gene 29 | −2.09 | 0.01 |
| IGHV3-74 | Immunoglobulin Heavy Variable 3-74 | −2.17 | 0.02 |

Genes expressed differentially according to ultrasound imaging phenotype—Contrast-enhanced ultrasound_Perfusion defect Of the B-mode ultrasound imaging phenotypes, orientation showed the most upregulated genes related to breast cancer. Breast cancers with nonparallel orientation showed overexpression of TFF1, AREG, AGR3, TFF3, and LINC00993 compared with those with parallel orientation. FIG. 1 shows gene expression data according to orientation by using a heat map and a volcano plot.

At SMI, the complex vessel morphology of cancer was related to the upregulation of FZD8 and the downregulation of IGF1R, NMI, and CRIPAK. The presence of a penetrating vessel at SMI was related to the upregulation of CST1 and the downregulation of CRIPAK. Elevated vascular index was related to the upregulation of MIR1307 and HIST2H2BE and the downregulation of MIR597.

At CEUS, the enhancement order was related to the downregulation of SNHG12 and VTRNA2-1. The enhancement margin was related to the upregulation of TFF1, STC2, and HOXB5 and the downregulation of PHLDA2. At the CEUS examination, the presence of the penetrating vessel was related to the upregulation of AGR2. FIG. 2 shows gene expression data according to the presence of penetrating vessel at CEUS by using a heat map and a volcano plot.

Gene Network Identification

Figure 3A:
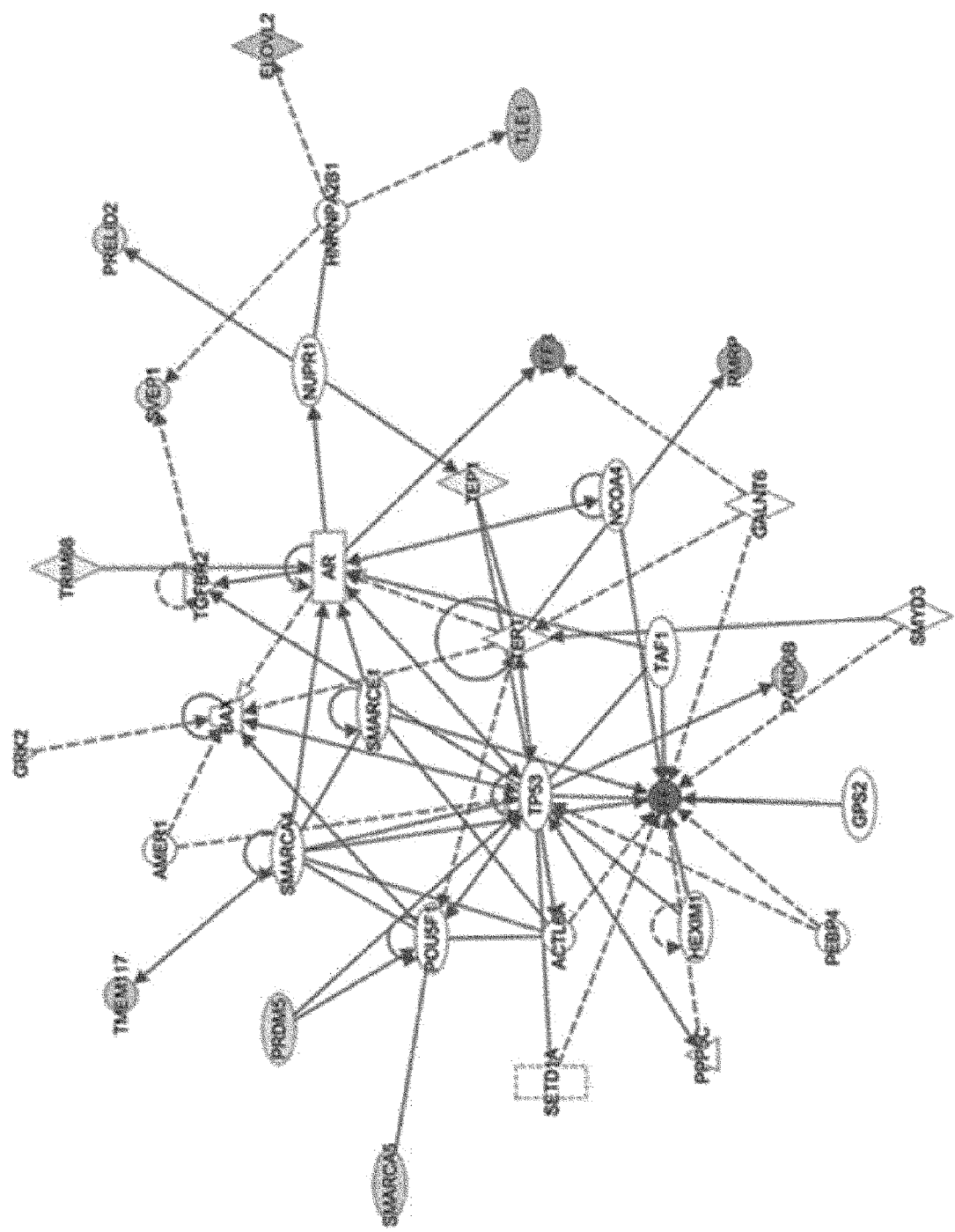
FIGS. 3A and 3B are drawings showing interactions between the top 100 differentially expressed genes according to the orientation at B-mode ultrasound imaging according to an example of the present disclosure.
Figure 3B:
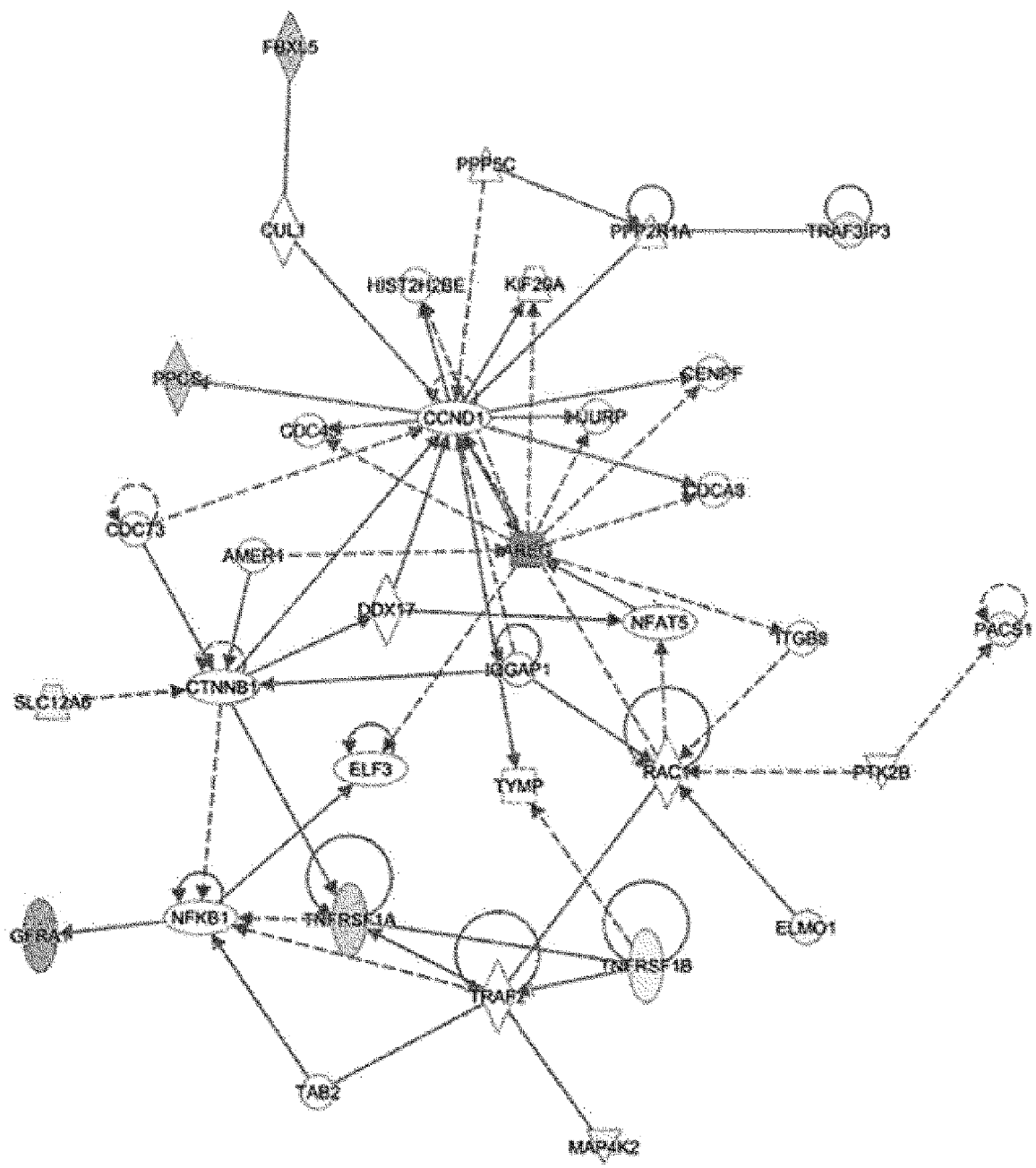

The top 100 differentially expressed genes according to each ultrasound imaging phenotype were used to identify gene networks based on the Ingenuity Pathways Knowledge Base. FIG. 3 shows the top two networks according to the orientation on B-mode ultrasound imaging. The top network with a score of 29 including TFF1, TFF3, TP53, TGFBR2, AR, BAX, TERT, and POUF51 genes was associated with cell cycle, cellular growth and proliferation, and cancer. TFF1 and TFF3 show direct interactions with TP53 and AR, respectively. The second highest scoring network with a score of 21 including AREG, CCND1, NFKB1, and RAC1 genes was associated with cancer, organismal survival, and injury.

The top network of penetrating vessels at CEUS images with a score of 18 included genes of AGR2, EGFR, EGR1, FOXA1, Mek, MAPK1, and AREG and was associated with cellular movement, organismal survival, and cell cycle.

The top network of vessel morphology at SMI with a score of 13 included genes of IGF1R, ESR1, IRS-1, RARA, FOXO1, NR3C1, HDAC2, and histone h3 and the functions thereof were associated with cell death and survival, and cancer.

Gene Function Analysis

Enriched functional annotations of expression profiles were obtained from ingenuity pathway analysis with an input of the top 100 differentially expressed genes according to each ultrasound imaging phenotype. The functions associated with general cancer or breast cancer were mainly related to the orientation on B-mode ultrasound imaging and the vessel morphology at SMI, and the results are shown in Table 3.

Enriched functions of significantly upregulated genes (TFF3, TFF1, and AREG) in nonparallel cancers included transformation of carcinoma cells, bending of DNA, cell movement, migration of cells, activation of epithelial cells, and mitosis of epithelial cell lines. Enriched functions of significantly up- or down-regulated genes (FZD8, IGF1R, and CRIPAK) in cancer with complex vessel morphology included proliferation of epithelial cells, repair of DNA, attachment, aggregation, anoikis, and growth inhibition.

TABLE 15

| Functional Annotation | P Value | Molecules |
|---|---|---|
| Transformation of carcinoma cells | <0.0032 | TFF3 |
| Bending of DNA | 0.0097 | TFF1 |
| Cell movement | 0.0105 | AREG, ELMO1, IGHV4-34, IGKV1-12, IGKV2-28, IGKV3-20, IGLV1-51, IGLV2-14, PARD6B, SLC12A6, TFF1, TFF3, TNFRSF1A, TNFRSF1B |

TABLE 15-continued

| Functional Annotation | P Value | Molecules |
|---|---|---|
| Migration of cells | 0.0235 | AREG, ELMO1, IGHV4-34, IGKV1-12, IGKV2-28, IGKV3-20, IGLV1-51, IGLV2-14, PARD6B, TFF1, TNFRSF1A, TNFRSF1B |
| Activation of epithelial cells | 0.0288 | AREG |
| Mitosis of epithelial cell lines | 0.0414 | AREG |

Functional analysis of differentially expressed genes according to ultrasound phenotype (orientation)

TABLE 16

| Functional Annotation | P Value | Molecules |
|---|---|---|
| Apoptosis of adenocarcinoma cell lines | <0.0102 | IGF1R, SNHG20 |
| Cell proliferation of adenocarcinoma cell lines | <0.0112 | IGF1R, SNHG20 |
| Depression of RNA | <0.0114 | UBB |
| Attachment of breast cancer cell lines | <0.0142 | IGF1R |
| Aggregation of breast cancer cell lines | <0.0170 | IGF1R |
| Polyploidization of tumor cell lines | 0.0111 | IGF1R |
| Transformation of carcinoma cell lines | 0.0111 | IGF1R |
| Repair of DNA | 0.0161 | HIST1H4D, IGF1R, UBB |
| Double-stranded DNA break repair | 0.0185. | HIST1H4D, IGF1R |
| Proliferation of epithelial cells | 0.0252 | FZD8, IGF1R |
| Anoikis of breast cancer cell lines | 0.0262 | IGF1R |
| Signal transduction | 0.0265 | CCR3, GNAT3, HTR1A, IGF1R, RXFP2 |
| Breast cancer | 0.0311 | ATAD2B, CRIPAK, FZD8, GLI2, HBA1/HBA2, HIST1H4D, IGF1R, NFIL3, PCSK5 |
| Global genomic repair | 0.0357 | UBB |
| Contact growth inhibition of breast cancer cell lines | 0.0371 | IGF1R |

Functional annotation of differentially expressed genes according to ultrasound phenotype (vessel morphology)

Analysis of Pathways Associated with Genes and Diseases of Interest

To determine significantly changed signal pathways, canonical pathway analyses were performed on the basis of functional annotation of the top 100 differentially expressed genes according to each ultrasound imaging phenotype by using corresponding bibliographic data. Ingenuity pathways technical data were used as a reference set. As shown in Table 4, several canonical pathways associated with cancer or breast cancer were identified regarding orientation and vessel morphology.

The AREG associated with orientation at B-mode ultrasound imaging was related to human HER2 signaling in breast cancer and ErbB signaling in canonical pathway analysis. The FZD8 or NMI associated with vessel morphology at SMI was related to Wnt/b-catenin signaling, PCP pathway, Wnt/Ca+ pathway, prolactin signaling, regulation of epithelial-mesenchymal transition pathway, and molecular mechanisms of cancer.

TABLE 17

| Ingenuity Canonical Pathway | −log (P value) | Ratio | Molecules |
|---|---|---|---|
| HER-2 Signaling in Breast Cancer | 1.41 | 0.0208 | PARD6B, AREG |
| Breast Cancer Regulation by Stathmin1 | 0.824 | <0.0195 | CALML5, PPM1J |
| ErbB Signaling | 0.538 | <0.0195 | AREG |

Canonical pathway of differentially expressed genes according to ultrasound phenotype (orientation)

TABLE 18

| Ingenuity Canonical Pathway | −log (P value) | Ratio | Molecules |
|---|---|---|---|
| PTEN Signaling | 1.9 | 0.0163 | IGF1R, MAGI3 |
| Wnt/β-catenin Signaling | 1.63 | 0.0118 | FZD8, UBB |
| DNA Methylation and Transcriptional Repression Signaling | 1.33 | 0.0294 | HIST1H4D |
| PCP pathway | 1.09 | 0.0167 | FZD8 |
| Wnt/Ca+ pathway | 1.09 | 0.0164 | FZD8 |
| Toll-like Receptor Signaling | 1 | 0.0133 | UBB |
| Myc Mediated Apoptosis Signaling | 0.991 | 0.013 | IGF1R |
| Growth Hormone Signaling | 0.943 | 0.0116 | IGF1R |
| Estrogen-Dependent Breast Cancer Signaling | 0.943 | 0.0116 | IGF1R |
| Prolactin Signaling | 0.921 | 0.011 | NMI |
| GABA Receptor Signaling | 0.91 | 0.0106 | UBB |
| NER Pathway | 0.876 | <0.0198 | HIST1H4D |
| IGF-1 Signaling | 0.833 | <0.0190 | IGF1R |
| RhoA Signaling | 0.807 | <0.0183 | IGF1R |
| STAT3 Pathway | 0.772 | <0.0176 | IGF1R |
| Hereditary Breast Cancer Signaling | 0.724 | <0.0167 | UBB |
| NF-κB Signaling | 0.642 | <0.0154 | IGF1R |
| Regulation of the Epithelial-Mesenchymal Transition Pathway | 0.62 | <0.0151 | FZD8 |
| NRF2-mediated Oxidative Stress Response | 0.613 | <0.0150 | UBB |
| EIF2 Signaling | 0.575 | <0.0146 | IGF1R |
| Molecular Mechanisms of Cancer | 0.375 | <0.0126 | FZD8 |

Canonical pathway of differentially expressed genes according to ultrasound phenotype (vessel morphology)

Determination of Therapy Through Correlation Between Ultrasound Phenotypes and Genes Patients with the upregulation of TFF1, TFF3, AREG, and AGR3 genes among the breast cancer patients with non-parallel orientation at B-mode ultrasound were subjected to hormone therapy as targeted therapy for estrogen receptor (ER). The patients who received treatment showed good therapy response without recurrence at 4 years of follow-up after therapy.

CONCLUSION

At B-mode ultrasound, it was identified that the nonparallel orientation of the cancer showed the upregulation of TFF1, TFF3, AREG, and AGR3. These genes were enriched in ER—positive breast cancers in the previous study. Additionally, TFF1, TFF3, and AGR3 were significantly associated with low tumor grades and proposed as early serum markers of breast cancer. From the results, nine (90%) of 10 cancers with nonparallel orientation revealed ER positivity, whereas 11 (52.4%) of 21 parallel cancers exhibited ER positivity. These results suggest that the nonparallel orientation at ultrasound might be associated with ER positivity and low tumor grades. AREG is involved in regulating ErbB signaling and may be a new target for breast cancer treatment. Our study similarly found that ErbB and HER-2 signals were related to AREG in canonical pathway analyses.

However, the action of TFF1 and TFF3 on disease prognosis is controversial. TFF1 and TFF3 are known to enhance stromal and lymphovascular invasion, resulting in increasing toxicity to lymph node metastases and distant metastases. From the results, the top network of the orientation including genes of TFF1 and TFF3 was associated with cell growth and proliferation. Therefore, these results are likely related to cancer progression and metastasis.

The complex vessel morphology including branches or branching vessels of tumor tissue is one of the malignant vascular features and might reflect tumor angiogenesis. From the results, complex vessel morphology at SMI was associated with the downregulation of the gene of CRIPAK and the upregulation of the gene of FZD8. Both the genes are related to tumor angiogenesis. CRIPAK is a negative regulator of PAK1, which promotes angiogenesis through increased permeability and vascular cell migration. In addition, PAK1 was related to tamoxifen therapy and resistance to tumor recurrence, and therefore is receiving attention as a therapeutic target. FZD8 was associated with the top network including VEGFA, a most significant gene in tumor angiogenesis. Another study reported that FZD8 plays a key role in drug resistance in triple-negative breast cancer through FZD8-mediated Wnt signaling and may be a potential target for improving therapeutic efficacy. Complex vessel morphology was associated with the downregulation of IGF1R, which is associated with low tumor grades, low metastasis capacity, and high overall survival. This study supported that the top networks of vessel morphology were associated with cancer and cell death. Therefore, complex vessel morphology in ultrasound images may be a predictor of tumor angiogenesis, tamoxifen therapy for luminal breast cancer, or chemotherapy and drug prognosis for triple-negative breast cancers.

Other vascular ultrasound imaging phenotypes were also associated with breast cancer-related genes. Penetrating vessels at SMI and CEUS were related to the upregulation of CST1 and AGR2, which promote breast cancer cell proliferation, metastasis, and low survival rates. Elevated vascular index at SMI was related to the upregulation of MIR1307 and HIST2H2BE, which are associated with drug resistance of breast cancer, and the downregulation of MIR597, which inhibits breast cancer cell proliferation and invasion. At CEUS, the centripetal enhancement of breast cancer was related to the downregulation of SNHG12 and VTRNA2-1, which act as tumor inhibitors. At CEUS, the uncircumscribed breast cancer margin was related to the upregulation of TFF1 and HOXB5, which are associated with metastasis or invasion of breast cancer, and the downregulation of PHLDA2, a tumor inhibition gene.

What is claimed is:

1. A method for providing information for choosing a breast cancer therapy by using an ultrasound image of breast cancer, the method comprising:
   a phenotype determination step of determining a phenotype of a breast tumor by using an ultrasound image;
   a gene information determination step of determining at least one gene information related to the breast cancer by using the phenotype of the breast tumor; and
   a therapy determination step of determining an individual breast cancer therapy by correlating the determined at least one gene information with gene information associated with the breast cancer therapy, wherein the ultrasound image is a B-mode ultrasound image, wherein the phenotype determined through the B-mode ultrasound image includes size, shape, orientation, margin, and calcifications of the breast tumor, wherein the size is related to at least one gene selected from the group consisting of MIR941-1, IGLV6-57, HIST1H1B, HIST1H31, ADH1B, PLIN4, and LUZP6;

the shape is related to at least one gene selected from the group consisting of MIR941-1, ZFP36L1, SNHG9, H2AFY2, POTEI, UBE2Q2L, FABP7, IGHV3-43, IGKJ5, and IGKJ2;

the orientation is related to at least one gene selected from the group consisting of TFF1, AREG, AGR3, TFF3, LINC00993, IGKV2-28, IGLV1-51, IGHV3-73, IGKV3-20, IGLV2-14, IGKV1-12, IGHV4-61, IGKV3D-15, IGHV1-3, IGHV4-4, IGHV1-18, IGHV4-34, IGHV3-74, CALML5, IGHJ5, and IGKJ2;

the margin is related to HLA-C gene; and the calcifications are related to at least one gene selected from the group consisting of CALML3, HIST1H4F, IGHV4OR15-8, CCL19, and IGLV8-61.

2. A method for providing information for choosing a breast cancer therapy by using an ultrasound image of breast cancer, the method comprising:

a phenotype determination step of determining a phenotype of a breast tumor by using an ultrasound image;

a gene information determination step of determining at least one gene information related to the breast cancer by using the phenotype of the breast tumor; and a therapy determination step of determining an individual breast cancer therapy by correlating the determined at least one gene information with gene information associated with the breast cancer therapy, wherein the ultrasound image is a superb microvascular imaging (SMI) ultrasound image, wherein the phenotype determined through the SMI ultrasound image includes vascular index, vessel morphology, and penetrating vessel, wherein the vascular index is a ratio of a number of pixels for a vascular signal to a number of pixels for the breast tumor, wherein the vascular index is related to at least one gene selected from the group consisting of IGHJ5, MIR1307, IGLV6-57, HLA-C, HIST2H2BE, CALML3, IGKV6-21, OR5P3, and MIR597;

the vessel morphology is related to at least one gene selected from the group consisting of HIST1H4D, TUSC1, FZD8, NMI, IGF1R, UBB, SERHL2, NFIL3, CRIPAK, SNHG20, HBA2, and SNHG12; and the penetrating vessel is related to at least one gene selected from the group consisting of HIST1H4D, CST1, TRBC2, SLC25A2, KRT14, MFAP4, IGKV2-40, NFIL3, POTEE, POTEI, ALDH3B2, CRIPAK, IGHJ2, AREG, and IGKJ5.

3. A method for providing information for choosing a breast cancer therapy by using an ultrasound image of breast cancer, the method comprising:

a phenotype determination step of determining a phenotype of a breast tumor by using an ultrasound image;

a gene information determination step of determining at least one gene information related to the breast cancer by using the phenotype of the breast tumor; and a therapy determination step of determining an individual breast cancer therapy by correlating the determined at least one gene information with gene information associated with the breast cancer therapy, wherein the ultrasound image is a contrast-enhanced ultrasound (CEUS) image, wherein the phenotype determined through the contrast-enhanced ultrasound image includes enhancement order, enhancement margin, internal homogeneity, penetrating vessel wherein the enhancement order is related to at least one gene selected from the group consisting of IGKV1D-39, CCL3L3, IGHG4, IGKV1D-12, IGKV3D-11, SNHG12, CPB1, MIR562, and VTRNA2-1;

the enhancement margin is related to at least one gene selected from the group consisting of STH, TFF1, STC2, AMY2A, HOXB5, IGKV1D-39, PHLDA2, HIST1H2AJ, TRAV14DV4, HIST1H1A, CXCL10, ISG15, IGHV4-39, IGKV3D-15, HIST2H2BF, HIST1H2BM, IGKV2-28, IGHV3-21, CALML5, IGHV1-18, IGKV2-29, IGHG4, IGHJ4, IGHJ5, and IGKJ2;

the internal homogeneity is related to at least one gene selected from the group consisting of IGKJ5, HLA-DQA1, HIST1H1B, and IGHV3-74;

the penetrating vessel is related to at least one gene selected from the group consisting of AGR2, HIST1H2BI, IGHV4-4, IGLV3-25, IGKV1D-39, IGHV1-2, IGHV3-15, IGKV1-27, IGLV3-1, IGKV2-40, IGKV2D-40, IGHV1-18, HIST1H2AG, IGHV3-33, IGKV1-12, IGKV1-17, IGHG1, TRBV5-6, IGHG4, IGHV4-61, IGKV2-28, IGHV1-8, IGHV4-39, IGHV3-21, IGHV3-9, IGKV3D-15, MIR562, IGHV1-69, IGHV4-31, IGHV1-3, and OR2J3.

* * * * *